(12) United States Patent
Nagata et al.

(10) Patent No.: US 8,991,240 B2
(45) Date of Patent: Mar. 31, 2015

(54) METHOD AND DEVICE FOR MEASURING BASIS WEIGHT AND MOISTURE CONTENT AMOUNT

(75) Inventors: Shinichi Nagata, Hyogo (JP); Hidetada Sawamoto, Hyogo (JP); Masahiro Kurosawa, Hyogo (JP)

(73) Assignee: Oji Holdings Corporation, Tokyo (JP)

( * ) Notice: Subject to any disclaimer, the term of this patent is extended or adjusted under 35 U.S.C. 154(b) by 466 days.

(21) Appl. No.: 13/574,856

(22) PCT Filed: Sep. 21, 2010

(86) PCT No.: PCT/JP2010/066286
§ 371 (c)(1),
(2), (4) Date: Oct. 11, 2012

(87) PCT Pub. No.: WO2011/092889
PCT Pub. Date: Aug. 4, 2011

(65) Prior Publication Data
US 2013/0025350 A1 Jan. 31, 2013

(30) Foreign Application Priority Data

Jan. 28, 2010 (JP) .................. 2010-016546

(51) Int. Cl.
 *G01N 5/02* (2006.01)
 *G01N 22/04* (2006.01)
 *G01N 33/34* (2006.01)
(52) U.S. Cl.
 CPC .............. *G01N 22/04* (2013.01); *G01N 33/346* (2013.01)
 USPC ................. 73/73; 324/633; 324/634
(58) Field of Classification Search
 CPC ..... G01N 33/346; G01N 22/04; G01N 22/00; G01N 33/246

USPC .............. 73/159, 73; 324/640, 639, 634, 633, 324/637
See application file for complete search history.

(56) References Cited

U.S. PATENT DOCUMENTS 3,829,764 A * 8/1974 Bosisio ..................... 324/632
7,362,108 B2 * 4/2008 Talanov et al. ............ 324/636
(Continued)

FOREIGN PATENT DOCUMENTS

CN 1826522 A 8/2006
CN 100458424 C 2/2009
(Continued)

OTHER PUBLICATIONS

Sasaki, Hiroshi, "Moisture, basis weight and thickness control of sheet material using a microwave cavity resonator", Nonwovens Review, Feb. 2, 1993, pp. 62-69, vol. 3 No. 3; cited in ISR.
Sawamoto, Hidetada et al., "Development of On-line Fiber Orientation Sensor System (Dielectric Type)", Japan TAPPI Journal, Jan. 2006, pp. 83-91, vol. 60 No. 1; cited in ISR, w/English abstract.
International Search Report of PCT/JP2010/066286, mailing date Nov. 9, 2010.

(Continued)

*Primary Examiner* — John Fitzgerald
*Assistant Examiner* — Marrit Eyassu
(74) *Attorney, Agent, or Firm* — Westerman, Hattori, Daniels & Adrian, LLP

(57) ABSTRACT

A resonance frequency shift amount $\Delta f$ and a peak level change amount $\Delta P$ are measured using a microwave resonator, V1 and V2 are obtained based on $V1=(\Delta f \cdot \epsilon''2/Kf - \Delta P \cdot \epsilon'2/Kp)/(\epsilon'1 \cdot \epsilon''2 - \epsilon''1 \cdot \epsilon'2)$, and $V2=(\Delta f \cdot \epsilon''1/Kf - \Delta P \cdot \epsilon'1/Kp)/(\epsilon'1 \cdot \epsilon''2 - \epsilon'1 \cdot \epsilon''2)$, and an absolute dry basis weight and a moisture amount are obtained based on absolute dry basis weight=$\beta \cdot V1$, and moisture amount=$\gamma \cdot V2$. For the constants Kf, Kp, $\epsilon'1$, $\epsilon'2$, $\epsilon''1$ and $\epsilon''2$, the constants $\epsilon'1$, $\epsilon'2$, $\epsilon''1$ and $\epsilon''2$ are determined so that the variance values of Kf and Kp are smaller than a predetermined value.

10 Claims, 17 Drawing Sheets

(56) References Cited

U.S. PATENT DOCUMENTS

2006/0288782 A1* 12/2006 Sawamoto et al. ............. 73/579
2007/0018657 A1* 1/2007 Nagata et al. ................. 324/636

FOREIGN PATENT DOCUMENTS

| | | |
|---|---|---|
| JP | 2006-349425 A | 12/2006 |
| JP | 2009-058379 A | 3/2009 |
| WO | 98/44339 A1 | 10/1998 |
| WO | 2006/123017 A1 | 11/2006 |
| WO | 2006/134237 A1 | 12/2006 |

OTHER PUBLICATIONS

Chinese Office Action dated Jan. 22, 2014, issued in corresponding Chinese Patent Application No. 201080062611.9 with partial English translation (8 pages).

Guoyu, "Microwave Dual-mode Sensor for Measuring Water Content of Paper", Academic Journal of Chemgdu Institute of Radio Engineering, Supplement 2, p. 153, 1988, with English translation.

* cited by examiner

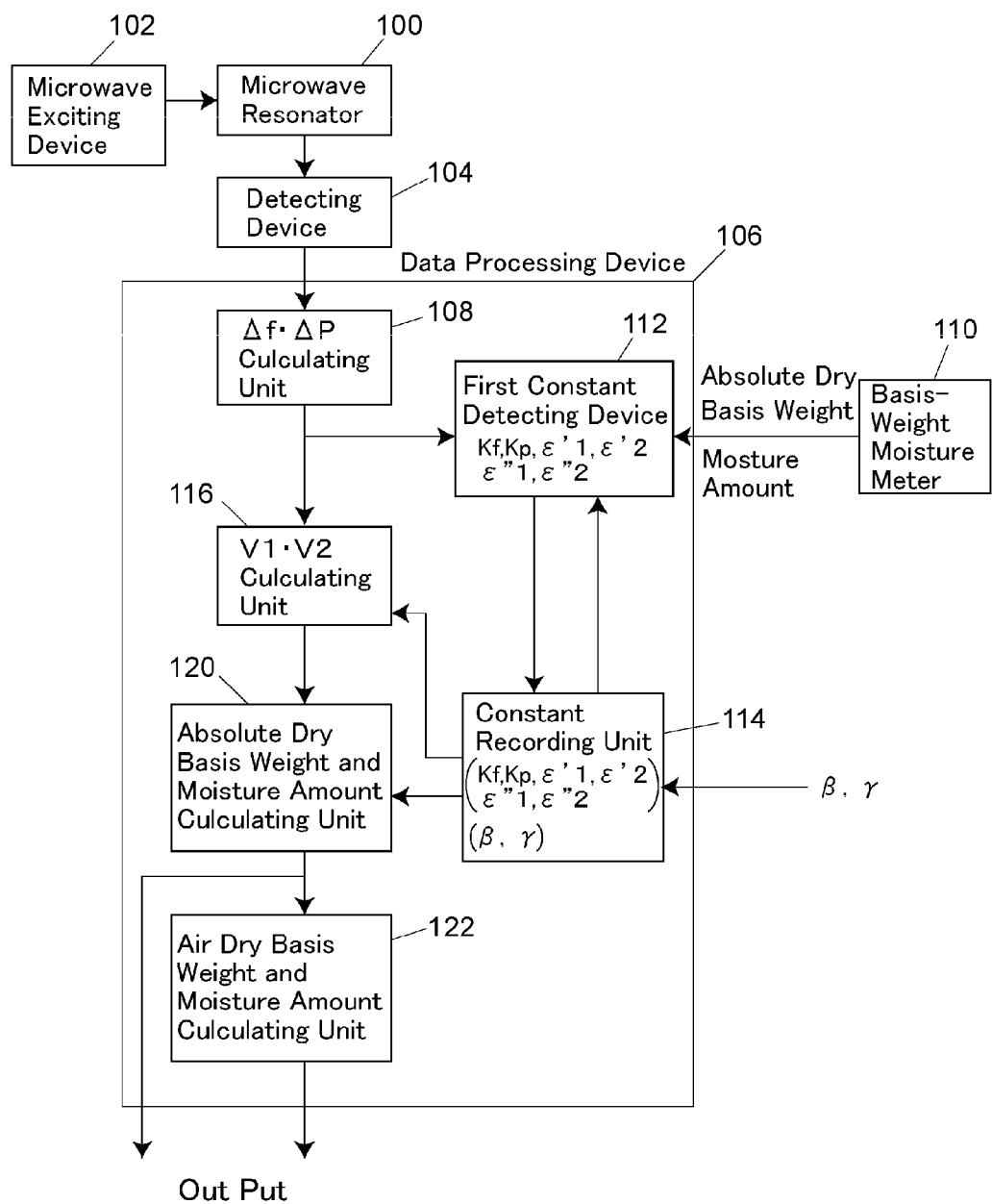

Fig. 20
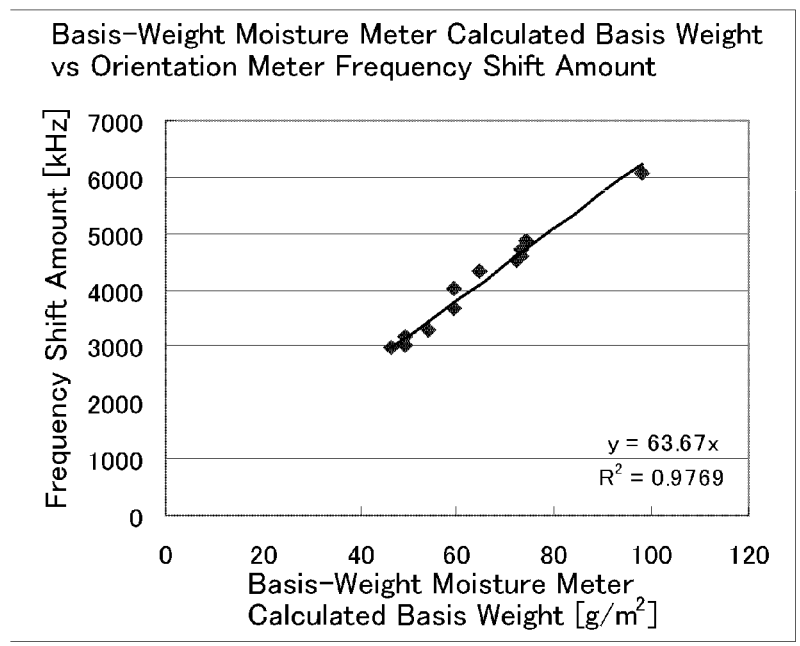
↓ Multiply Coefficient
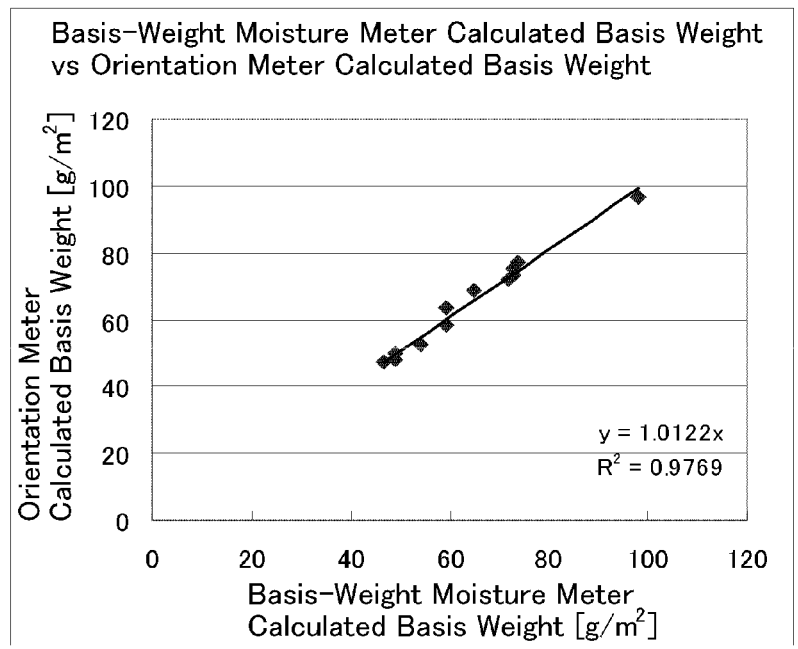

METHOD AND DEVICE FOR MEASURING BASIS WEIGHT AND MOISTURE CONTENT AMOUNT

TECHNICAL FIELD

The present invention relates to a method and an apparatus for online measurement of a basis weight (weight per square meter) and a moisture content amount of a sheet-like material, in particular, a paper sheet.

BACKGROUND ART

In a manufacturing process of paper, online measurement of a basis weight (weight per square meter) and a moisture percentage is very important, and the basis weight is an important control item in terms of both paper quality and conducting business. Conventionally, it is common to use a basis-weight moisture meter (Basis Weight & Moisture Measurement System) to obtain a basis weight of paper from a transmission attenuation amount of beta rays, and paper moisture from an absorbed amount of near infrared rays. Basis weight values measured by a basis-weight moisture meter are known to have the highest reliability.

In order to measure a basis weight, beta rays obtained from a radioactive radiation source such as Kr85 (krypton) or Pm147 (promethium) are used. An attenuation amount of the beta rays is large if the basis weight is large, and the attenuation amount thereof is small if the basis weight is small, and therefore, a transmission amount of the beta rays and the basis weight are almost inversely proportional to each other. In order to obtain an accurate basis weight, a calibration curve representing relation between the transmission amount of the beta rays and the basis weight is used.

Near infrared rays commonly used for measurement of moisture are three types of lights: base light, measured light, and corrected light. A wavelength of the base light is 1.8 μm, and light of this wavelength is not attenuated by moisture. A wavelength of the measured light is 1.9 μm, and light of this wavelength is attenuated by moisture. A wavelength of the corrected light is 2.1 μm, and light of this wavelength is not susceptible to an influence of cellulose. It is possible to obtain an accurate moisture amount by previously examining the relation between an attenuation amount of the measured light due to moisture and a moisture amount as a calibration curve.

Since the beta rays are used in the basis weight measurement using a conventional basis-weight moisture meter, it is necessary to use a radioactive radiation source, such as krypton 85 or promethium 147 as a radiation source. A radioactive radiation source can have harmful effects on a human body. Therefore, in the measurement, a restricted area is provided to keep off a radiation source, a person who frequently works near the radiation source is obligated to carry a film badge, and it is required to check an exposed radiation dose on regular basis. Further, it is required to place a licensed engineer for radiation protection, and great care and specialized knowledge are required for radiation protection.

As a method of avoiding such a problem due to the use of a radioactive radiation source, the present inventors have proposed a method of measuring a basis weight and a moisture of a sheet-like material, such as paper, without using radioactive rays (see Patent Document 1). The proposed method is of measuring a basis weight and a moisture at the same time using a microwave dielectric resonator, and shows that, as an application of an apparatus for online measurement of dielectric anisotropy of a sample such as fiber orientation of paper, it is possible to measure a basis weight and a moisture amount at the same time besides fiber orientation. According to the proposed method, a basis weight is obtained from a resonance frequency shift amount which is a difference between a resonance frequency without a sample and a resonance frequency with a sample provided, and a moisture amount is obtained from a resonance peak level change amount which is a difference between a peak level of the resonance frequency without a sample and a peak level of the resonance frequency with a sample provided.

PRIOR ART DOCUMENT

Patent Document

Patent Document 1: JP 2006-349425 A (U.S. Pat. No. 7,423,435 B2)

SUMMARY OF THE INVENTION

Problems to be Solved by the Invention

It has been found that when measuring a basis weight and a moisture amount at the same time based on the proposed method using a microwave dielectric resonator, if the moisture amount is constant, it is possible to measure the basis weight at very high measurement accuracy as illustrated in FIG. 19. FIG. 19 is a chart illustrating a result of an online measurement while supplying an elongated paper sample to the microwave dielectric resonator at a speed of 760 m/min, and the measurement is made at a portion at which the basis weight changes from 60.0 g/m$^2$ to 49.3 g/m$^2$ while the moisture amount is kept constant.

Further, when the moisture amount is constant, as illustrated in an upper chart in FIG. 20, a strong correlation can be observed between a resonance frequency shift amount and the measurement result of the basis weight by a basis-weight moisture meter for various paper brands having different basis weights. Accordingly, it appears that the basis weight can be accurately measured as illustrated in a lower chart in FIG. 20 by multiplying the resonance frequency shift amount by a coefficient.

It, however, has become apparent that when measuring a basis weight using a microwave resonator, a value of the measured basis weight is susceptible to the moisture amount not only with a dielectric resonator, but also with a cavity resonator. For example, FIG. 21 is a display screen when the basis weight and the moisture percentage are online measured in the same manner as in FIG. 19 using a dielectric resonator. In this case, when the moisture percentage has changed from 2.7% to 5.8%, the measured value of the basis weight also changes even though the sample is paper having a constant basis weight. The basis weight shown in the display screen in FIG. 21 is calculated as being proportional to the resonance frequency shift amount, and the moisture percentage is calculated from the resonance peak level change amount. Moreover, FIG. 21 also shows a measurement result of a basis weight (B) and a moisture percentage (M) measured by a basis-weight moisture meter for comparison.

It is to be noted that, as used herein, terms "moisture percentage" and "moisture amount" relating to an amount of moisture carry equivalent meaning, and "moisture percentage" and "moisture amount" are expressed in the following expression:

Moisture Percentage=(Moisture Amount/(Absolute Dry Basis Weight+Moisture Amount)×100(%)

(where an absolute dry basis weight is the basis weight when the moisture percentage is 0%).

An object of the present invention is to provide an accurate measurement of a basis weight while eliminating an influence of a moisture amount (moisture percentage) when measuring the basis weight using a microwave resonator.

Means for Solving the Problems

As a result of an investigation, it is considered that the basis weight is susceptible to an influence of the moisture amount in a basis weight measurement using a microwave resonator, because the basis weight is calculated based on a resonance frequency shift amount proportional to a product of a value subtracting 1 from a dielectric constant of absolute dry paper (whose moisture percentage is 0) and paper thickness, and an influence of the moisture is not taken into account for the purpose of calculation. To the measurement result of resonance frequency shift amount, in addition to a resonance frequency shift amount due to an absolute dry portion of the paper, a resonance frequency shift amount due to a dielectric constant of water is added. Since the dielectric constant of water is as high as about 80 at 4 GHz, an influence of the dielectric constant of water given to the result of the resonance frequency shift amount cannot be ignored.

Based on the findings, the present invention is to eliminate by calculation a resonance frequency shift amount generated due to the dielectric constant of water, and to eliminate an influence of moisture from a measured value of the basis weight.

First, an outline of an apparatus of measuring a basis weight and a moisture amount (or a moisture percentage) will be described.

When measuring a basis weight and a moisture amount of paper, and not fiber orientation of the paper, using a microwave resonator, it is required to cancel anisotropy of a dielectric constant. One example of a canceling method is to use, for example, a single microwave resonator. The microwave resonator may be either a cavity resonator or a dielectric resonator. In this case, when a cavity resonator is employed, such as a cylindrical cavity resonator or a spherical cavity resonator is used and a resonance mode in which an electric field vector is not biased in a certain direction is selected, for example, such as a $TE_{011}$ mode in which the electric field vector is in a loop shape. It should be appreciated that when a dielectric resonator is employed, it is desirable to select a resonance mode having an electric field distribution in which an electric field vector of an evanescent wave is directed in all directions using a columnar cavity resonator, or an electric field distribution in which the electric field vector is in a loop shape, instead of an electric field distribution in which the electric field vector is biased in a certain direction. In this case, it is possible to calculate a basis weight and a moisture amount directly using a resonance frequency shift amount and a resonance peak level change amount respectively obtained by a resonator with a sample and a resonator without a sample.

When a basis weight and a moisture amount are to be measured by an apparatus of online measuring dielectric anisotropy of a sample such as fiber orientation of paper as one application of such an apparatus, there is a problem that the measurement is by contrast subject to an influence of anisotropy of a dielectric constant of the sample. While the dielectric constant takes different values depending on directions as being tensor, values of the basis weight and the moisture amount do not change depending on directions as being scalar quantities. A problem to be solved is how to cancel anisotropy of a dielectric constant when a basis weight or a moisture amount is measured.

A method of canceling anisotropy of a dielectric constant of a sample using an apparatus for measuring the dielectric anisotropy will be described. FIG. 2A and FIG. 2B are schematic diagrams of a rectangular microwave dielectric resonator. FIG. 2A is a plan view, and FIG. 2B a vertical cross-sectional view taken along line passing through the antennas 2a, 2b. A dielectric resonator 1 is excited by the one antenna 2a and outputs an output from the other antenna 2b. The resonator 1 and the antennas 2a, 2b are housed within a shielding case 4.

While a major part of resonance energy is contained within the resonator 1, another part of the energy comes out on its surface as an evanescent wave. In a case of a rectangular dielectric resonator, by appropriately selecting a resonance mode, a distribution of an electric field coming out on the surface of the resonator is in parallel with a direction of a long side. Here, the resonator is used in a resonance mode in which the distribution of the electric field is in parallel with the direction of the long side. When almost all of electric field vectors of an evanescent wave 6 are parallel, it is possible to measure anisotropy of a dielectric constant, that is, orientation, of a sample 8.

When the sample 8 is placed near or on an upper surface of the dielectric resonator 1, a resonance frequency shifts to a low frequency side as illustrated in FIG. 3 according to a dielectric constant of the evanescent wave 6 in a direction of the electric field vectors. An amount of this resonance frequency shift is taken as $\Delta f$. The resonance frequency shift amount is defined to be a value obtained by subtracting a resonance frequency in a case with a sample from a resonance frequency in a blank period in a case without a sample.

When the sample 8 is placed near or on an upper surface of the dielectric resonator 1, a peak level at a resonance frequency position decreases according to a dielectric loss factor of the sample at the same time as the resonance frequency shifts. An amount of this peak level change is taken as $\Delta P$. The peak level change amount is defined to be a value obtained by subtracting a peak level at a resonance frequency position in a case with a sample from a peak level at a resonance frequency position in a blank period in a case without a sample. Where a dielectric constant of the sample is $\in'$, a dielectric loss factor is $\in''$, and a sample thickness is T, the frequency shift amount $\Delta f$ is proportional to $(\in'-1) \times T$, and the peak level change amount $\Delta P$ is proportional to $\in'' \times T$.

When measuring the orientation, it is sufficient to check the anisotropy of the dielectric constant. Therefore, it is possible to learn the anisotropy of the dielectric constant by placing a plurality of rectangular dielectric resonators so that directions of the resonators are different from each other, and by detecting resonance frequency shift amounts of the respective resonators.

FIG. 4 shows an example of a layout of the resonators in a case, in which five rectangular dielectric resonators 1a to 1e are provided in such a way that the resonators have directions ($\theta$) different from each other with respect to a reference direction. It is preferable that the five resonators 1a to 1e are in proximity of each other so as to be able to measure at a position as close as possible. In this example, the five resonators 1a to 1e are provided within a circle having a diameter of 200 mm. Here, a movement direction of the sample (MD direction) is taken as the reference direction as one example, while the reference direction can be freely determined.

FIG. 5 shows an orientation pattern corresponding to this example. This pattern is obtained by plotting on a polar coordinate (r, $\theta$) in which an angle is $\theta$ and a distance from the point of origin is r, taking the resonance frequency shift amount Δf detected by each resonator as r and a direction of each of the resonators 1a-1e (θ) as an angle θ, and then performing ellipse approximation. Since a long axis direction of the ellipse represents a maximum direction of the frequency shift amount, a dielectric constant of the sample is maximized in this direction. This means that fibers or molecular chains are oriented in this direction. The long axis direction of the ellipse is a degree angle (φ). By contrast, a degree of orientation can be expressed by a difference or a ratio between a long axis a and a short axis b of an approximated ellipse.

The invention described in Patent Document 1 is contrived as a sideshow of a method and an apparatus of obtaining a fiber orientation or a molecular orientation of sheet-like material such as paper based on anisotropy of a dielectric constant, and able to measure a basis weight at the same time as the orientation. Therefore, when measuring the basis weight as a scalar quantity, directional dependency of the dielectric constant adversely become an obstacle. When plotting the resonance frequency shift amount on the polar coordinate, if the sample is not non-oriented, the resonance frequency shift amount takes different values as illustrated in FIG. 5, for example, according to directional dependency of the dielectric constant of the sample. However, the basis weight does not have directional dependency since the basis weight is scalar.

A first method of canceling directional dependency of a resonance frequency shift amount due to the anisotropy of the dielectric constant is to simply performing averaging procedure of resonance frequency shift amounts of the plurality of resonators.

A second method of canceling directional dependency is to take a radius of a circle having the same area as an area of an ellipsoidal body obtained by plotting the resonance frequency shift amount Δf on the polar coordinate as illustrated in FIG. 5 and by performing ellipse approximation as a converted shift amount Δfr after canceling the dielectric anisotropy of the sample. For example, a plurality of rectangular dielectric resonators are provided only on one side of a sheet-like sample in the same plane such that long sides of the resonators are oriented to the directions (θ) different from each other with respect to the reference direction, resonance frequencies $f_1$ to $f_n$ of the resonators are respectively measured, and resonance frequency shift amounts $\Delta f_1$ to $\Delta f_n$ for one sample of the rectangular dielectric resonators are respectively obtained. As defined previously, the shift amounts $\Delta f_1$ to $\Delta f_n$ are differences between a resonance frequency $f_0$ in a case without a sample and the resonance frequencies $f_1$ to $f_n$ of the rectangular dielectric resonators in a case with a sample, respectively. Next, plotting is performed on the polar coordinate (r, θ) in which the angle is θ and the distance from the point of origin is r, taking the direction (θ) as an angle θ and the shift amounts $\Delta f_1$-$\Delta f_n$ as r, an ellipse is drawn by the ellipse approximation process as illustrated in FIG. 5, and an area of the ellipse is obtained. Then, a radius of a circle having the same area as the area of the ellipse is obtained, and the radius thereof corresponds to a resonance frequency shift amount after canceling the anisotropy.

The following description assumes that the frequency shift amount Δf after canceling the dielectric anisotropy is obtained based on one of the above methods.

(Basic Concept)

When using a microwave resonator, the resonance frequency shift amount Δf and the resonance peak level change amount ΔP are shown as illustrated in FIG. 3 depending on presence of a sample. Where the sample thickness is T, the resonance frequency shift amount Δf is proportional to ((dielectric constant−1)×T), and the resonance peak level change amount ΔP is proportional to (dielectric loss factor×T). This principle is derived based on the perturbative theory as described in Patent Document 1.

When considering a model in which paper is divided into an absolute dry portion and water as illustrated in FIG. 6, and taking a volume of the absolute dry portion to be measured as V1 and a volume of water as V2, expressions listed below are established based on this principle.

$$\Delta f = Kf(V1 \cdot \in'1 + V2 \cdot \in'2) \quad (1)$$

$$\Delta P = Kp(V1 \cdot \in''1 + V2 \cdot \in''2) \quad (2)$$

In the expressions, Δf: resonance frequency shift amount;
ΔP: Resonance Peak Level Change Amount;
V1: Volume of Absolute Dry Paper Under Certain Condition;
V2: Volume of Water Under Certain Condition;
Kf: Proportional Constant For Matching Dimensions;
Kp: Proportional Constant For Matching Dimensions;
$\in'1$: Dielectric Constant of Absolute Dry Paper−1;
$\in'2$: Water Dielectric Constant;
$\in''1$: Dielectric Loss Factor of Absolute Dry Paper; and
$\in''2$: Dielectric Loss Factor of Water (varies depending on a frequency, a degree of binding, and a temperature).

V1 is a value proportional to an absolute dry basis weight, and V2 is a value proportional to a moisture amount. The expression 1 indicates that the resonance frequency shift amount is obtained as a sum of the dielectric constant of the absolute dry portion of the paper and the dielectric constant of the water. Likewise, the expression 2 indicates that the peak level change amount ΔP is obtained as a sum of the dielectric loss factor of the absolute dry portion of the paper and the dielectric loss factor of the water.

Kf and Kp are proportional constants attributable to the apparatus, and take constant values. Kf and Kp also define conversion of dimensions and an area of measurement.

Solving the expressions 1 and 2 for V1 and V2, expressions listed below are obtained.

$$V1 = (\Delta f \cdot \in''2/Kf - \Delta p \cdot \in'2/Kp)/(\in'1 \cdot \in''2 - \in''1 \cdot \in'2) \quad (3)$$

$$V2 = (\Delta f \cdot \in''1/Kf - \Delta p \cdot \in'1/Kp)/(\in''1 \cdot \in'2 - \in'1 \cdot \in''2) \quad (4)$$

Here, while $\in'1$, $\in'2$, $\in''1$, and $\in''2$ are material constants, these constants as well as Kf and Kp are determined as apparatus constants in the present invention. Specifically, the constants Kf, Kp, $\in'1$, $\in'2$, $\in''1$, and $\in''2$ are determined based through Steps A and B described below.

(Step A) For each of a plurality of standard samples having different basis weights or moisture amounts, a resonance frequency shift amount Δf and a peak level change amount ΔP are measured by a measurement apparatus using a microwave resonator, and an absolute dry basis weight (BD) and a moisture amount (WT) are measured by a basis-weight moisture meter.

Between V1 and the absolute dry basis weight (BD), and V2 and the moisture amount (WT), the following relations are respectively established.

$$\text{Absolute Dry Basis Weight}(BD) = \beta \cdot V1 \quad (5)$$

$$\text{Moisture Amount}(WT) = \gamma \cdot V2 \quad (6)$$

In the expressions, β and γ are proportional constants. The constant β is a specific gravity of an absolute dry paper, and is obtained in advance. As one example, it is assumed that β=0.85. The constant γ is a specific gravity of the water, and it can be assumed that γ=1.

(Step B) Taking V1=BD/β using the absolute dry basis weight (BD) and V2=WT/γ using the moisture amount (WT) obtained by the basis-weight moisture meter in Step A, and using Δf and ΔP obtained in Step A, ∈'1, ∈'2, ∈"1, and ∈"2 when variance values of Kf and Kp are smaller than a predetermined value in the relation of the expressions 3 and 4 are obtained. It is possible to assume that γ=1, and V2=WT.

Here, as the expressions 3 and 4 are derived from the expressions 1 and 2, the expressions 3 and 4 are equivalent to the relation of the expressions 1 and 2.

As a preferred aspect of a method of determining the constants Kf, Kp, ∈'1, ∈'2, ∈"1, and ∈"2, Kf and Kp are calculated while changing the constants ∈'1, ∈'2, ∈"1, and ∈"2 under appropriate constraint conditions, and a combination of Kf, Kp, ∈'1, ∈'2, ∈"1, and ∈"2 when the variance values of Kf and Kp are smaller than a predetermined value for all the standard samples that have been measured is taken as apparatus constants for the measurement apparatus.

A determination operation of the constants Kf, Kp, ∈'1, ∈'2, ∈"1, and ∈"2 is performed for each measurement apparatus. In order to obtain a more accurate measurement result, it is preferable to perform the constant determination operation by preparing a plurality of samples, that is, for a different brand of paper, by preparing a plurality of standard samples of the brand, to determine the constants Kf, Kp, ∈'1, ∈'2, ∈"1, and ∈"2.

It is possible to perform an operation of converging each of variance values of Kf and Kp to be smaller than a predetermined value while changing the constants ∈'1, ∈'2, ∈"1, and ∈"2 by using an appropriate program on a computer. As one example of such a program, a program called "Solver" (one of the functions of the spreadsheet software "Excel" from Microsoft Corporation) can be used. The constraint conditions for determining the constants Kf, Kp, ∈'1, ∈'2, ∈"1, and ∈"2 using "Solver" are set as described below.

(1) Absolute Dry Paper Dielectric Constant ∈'1:

Since it is difficult to directly measure the dielectric constant ∈'1, it is considered that this constant is within a range listed below, determining based on a molecular structure of cellulose and an added inorganic substance (such as talc).

1.0<∈'1<20.0

(2) Dielectric Loss Factor of Absolute Dry Paper ∈"1:

Since it is difficult to directly measure the dielectric loss factor ∈"1, it is considered that this constant is within a range listed below, determining based on dielectric loss factors of various polymeric materials.

0<∈"1<1.0

(3) Water Dielectric Constant ∈'2:

A dielectric constant of completely unbound free water (free water) is on the order of 80 at normal temperature and 4 GHz, while the dielectric constant varies depending on the temperature and the frequency due to dielectric variance. However, a dielectric constant of water contained in food products or cement, also referred to as bound water or bond water, generally decreases as not being fully polarized (alternated) to an external electric field, although this depends on how the water molecules are bound by the surroundings. Therefore, it is considered that the water dielectric constant ∈'2 is within a range listed below.

1.0<∈'2<80

(4) Dielectric Loss Factor of Water ∈"2:

A peak of the dielectric loss factor of free water generally falls around 20 GHz (normal temperature), and a value at this time is on the order of 34. By contrast, a peak frequency for bound water generally shifts by about two digits to a low frequency side, although this depends on the circumstances. Accordingly, the dielectric loss factor of bound water at 4 GHz corresponds to a right shoulder of a frequency variance curve of the dielectric loss factor, and becomes considerably smaller than 34. Therefore, it is considered that the dielectric loss factor of water ∈"2 is within a range listed below.

0<∈"2<15

(5) The proportional constants Kf and Kp unique to the apparatus should be converged to one point on a chart when plotting based on various actual measured data, as being constant in nature. When variance of Kf and Kp satisfies conditions described below as converging conditions, it is considered that Kf and Kp are converged to constant values.

Variance of Kf<0.1

Variance of Kp<0.0001

The above values relating to the variance values of Kf and Kp are "predetermined values" relating to the variance values of Kf and Kp according to the present invention, and are previously set. When these predetermined values are set to large values, it is possible to decrease processing time for determining the constants, while accuracy of the basis weight and the moisture amount that are obtained as a result decreases. By contrast, when these predetermined values are set to small values, it is possible to improve the accuracy of the basis weight and the moisture amount that are obtained, while the processing time for determining the constants increases. The appropriately sized "predetermined values" are set considering the accuracy of the basis weight and the moisture amount that are obtained.

Under the above described constraint conditions, "Solver" is applied to the expression 1 and the expression 2, and the constants Kf, Kp, ∈'1, ∈'2, ∈"1, and ∈"2 are determined.

A combination of the material constants ∈'1, ∈'2, ∈"1, and ∈"2 derived for 38 paper samples of various types, when Kf and Kp satisfy the above condition (5), is as listed below.

∈'1 (Absolute Dry Paper Dielectric Constant-1)=4.0

∈'2 (Water Dielectric Constant)=29.95

∈"1 (Dielectric Loss Factor of Absolute Dry Paper)=0.210

∈"2 (Dielectric Loss Factor of Water)=9.71

Further, it becomes clear that plots of Kf and Kp are as illustrated in FIG. 7, substantially concentrating on a constant value. Respectively, average values of Kf and Kp in this case are listed as below:

Kf=10.843, and

Kp=0.1191.

Using the constants Kf, Kp, ∈'1, ∈'2, ∈"1, and ∈"2 thus determined, V1 and V2 are obtained using the expressions 3 and 4 based on the resonance frequency shift amount Δf and the peak level change amount ΔP measured for the measurement samples. Thus, the absolute dry basis weight (BD) and the moisture amount (WT) of the measurement sample are obtained by calculation using the expressions 5 and 6.

Further, the air dry basis weight and the moisture percentage are obtained by expressions listed below.

$$\text{Air Dry Basis Weight} = \text{Absolute Dry Basis Weight}(BD) + \text{Moisture Amount}(WT)(g/m^2) \quad (7)$$

$$\text{Moisture Percentage} = (\text{Moisture Amount}(WT)/\text{Air Dry Basis Weight}) \times 100(\%) \quad (8)$$

The constants Kf, Kp, ∈'1, ∈'2, ∈"1, and ∈"2 should be determined for each measurement apparatus, as being determined as the apparatus constants. The above values are unique to the apparatus that has performed the measurement, and a different measurement apparatus takes different values.

A method of measuring basis weight and moisture amount according to the present invention is for calculating a basis weight and a moisture amount of a sample constituted by a paper sheet using a microwave resonator, and the method includes the steps S1 to S6.

(Step S1)

A step of obtaining a resonance frequency and a resonance peak level of the microwave resonator in a case without a sample.

(Step S2)

A step of obtaining a resonance frequency and a resonance peak level of the microwave resonator in the case where the sample is measured.

(Step S3)

A step of obtaining a resonance frequency shift amount $\Delta f$ as a difference between the resonance frequency obtained in the step 1 and the resonance frequency obtained in the step 2.

(Step S4)

A step of obtaining a peak level change amount $\Delta P$ as a difference between the resonance peak level obtained in the step 1 and the resonance peak level obtained in the step 2.

(Step S5)

A step of obtaining V1 and V2 using the expressions 3 and 4 by which the constants Kf, Kp, $\in'1$, $\in'2$, $\in''1$, and $\in''2$ are determined.

(Step S6)

A step of obtaining an absolute dry basis weight and a moisture amount using the expressions 5 and 6.

In a preferred embodiment, an air dry basis weight and the moisture percentage are further obtained using the following expressions:

Air Dry Basis Weight=Absolute Dry Basis Weight+ Moisture Amount

Moisture Percentage=Moisture Amount×100/Air Dry Basis Weight

In the case where the method of measuring the basis weight and moisture amount according to the present invention is performed by an apparatus measuring dielectric anisotropy of a sample, a plurality of rectangular dielectric resonators constituting the microwave resonator are provided only on one side of a sample in the same plane such that long sides of the resonators are oriented to directions ($\theta$) different from each other. Then, taking the directions ($\theta$) as angles $\theta$ and the resonance frequency shift amounts $\Delta f_1$ to $\Delta f_n$ of the resonators as r, plotting on a polar coordinate (r, $\theta$) in which an angle is $\theta$ and a distance from the point of origin is r to draw an ellipse by an ellipse approximation process, obtaining a radius $\Delta fr$ of a circle having an area identical to an area of the ellipse, the obtained $\Delta fr$ is taken as $\Delta f$ in the expressions 3 and 4. Peak level change amounts $\Delta P_1$ to $\Delta P_n$ of the resonators are obtained, and one of $\Delta Pr(A)$, $\Delta Pr(B)$, and $\Delta Pr(C)$ is taken as $\Delta P$ in the expressions 3 and 4.

(A) $\Delta Pr$ constituted by one of $\Delta P_1$ to $\Delta P_n$.

(B) $\Delta Pr$ constituted by an average value of $\Delta P_1$ to $\Delta P_n$.

(C) $\Delta Pr$ constituted by a radius of a circle having an area identical to an area of an ellipse obtained by taking the directions ($\theta$) as angles $\theta$ and $\Delta P_1$ to $\Delta P_n$ as r, plotting on the polar coordinate (r, $\theta$) in which the angle is $\theta$ and a distance from the point of origin is r, and drawing the ellipse by the ellipse approximation process.

An apparatus of measuring basis weight and moisture amount according to the present invention includes, as illustrated in FIG. 1 showing a preferred embodiment, a microwave resonator (100); a microwave exciting device (102) configured to generate an electric field vector in the resonator; a detecting device (104) configured to detect one of a transmission energy and a reflected energy by the resonator (100); and a data processing device (106) configured to import resonance frequencies of the microwave resonator (100) and peak levels at positions of the resonance frequencies in cases without a sample and with a sample from the detecting device (104), and to calculate a basis weight and a moisture amount of the sample.

The data processing device (106) includes a $\Delta f \cdot \Delta P$ calculating unit (108), a first constant determining unit (112), a constant recording unit (114), a V1·V2 calculating unit (116), and an absolute dry basis weight and moisture amount calculating unit (120).

The $\Delta f \cdot \Delta P$ calculating unit (108) is configured to calculate a resonance frequency shift amount $\Delta f$ and a peak level change amount $\Delta P$ respectively based on the resonance frequencies and the peak levels imported from the detecting device (104).

The first constant determining unit (112) is configured to determine constants Kf, Kp, $\in'1$, $\in'2$, $\in''1$, and $\in''2$ by obtaining $\in'1$, $\in'2$, $-''1$, and $\in''2$ when variance values of Kf and Kp are smaller than a predetermined value in the relation of the expressions 3 and 4 (the same as the relation of the expressions 1 and 2), using $\Delta f$ and $\Delta P$ obtained by the $\Delta f \cdot \Delta P$ calculating unit (108) when each of a plurality of standard samples having different values for one of the basis weight and the moisture amount is measured by the microwave resonator (100), and taking an absolute dry basis weight (BD) as V1/$\beta$ and a moisture amount (WT) as V2/$\gamma$ by measuring the standard samples by a basis-weight moisture meter (110).

The constant recording unit (114) is configured to record the constants Kf, Kp, $\in'1$, $\in'2$, $\in''1$, and $\in''2$ determined by the first constant determining unit (112), and the proportional constants $\beta$ and $\gamma$ determined in advance.

The V1·V2 calculating unit (116) is configured to calculate V1 and V2 based on the expressions 3 and 4 using the constants Kf, Kp, $\in'1$, $\in'2$, $\in''1$, and $\in''2$ recorded in the constant recording unit (112), and $\Delta f$ and $\Delta P$ obtained by the $\Delta f \cdot \Delta P$ calculating unit (108) when the samples are measured by the microwave resonator (100).

The absolute dry basis weight and moisture amount calculating unit (120) is configured to calculate an absolute dry basis weight and a moisture amount based on the expressions 5 and 6 from V1 and V2 obtained by the V1·V2 calculating unit (116) when the measurement samples are measured by the microwave resonator (100) and the proportional constants $\beta$ and $\gamma$ recorded in the constant recording unit (114).

In a preferred embodiment, an air dry basis weight and moisture percentage calculating unit (122) configured to calculate an air dry basis weight and a moisture percentage based on the expressions according to claim 2 from the absolute dry basis weight and the moisture amount obtained by the absolute dry basis weight and moisture amount calculating unit (120) are provided.

When the apparatus also serves as an apparatus measuring dielectric anisotropy of the samples, the microwave resonator is constituted by a plurality of rectangular dielectric resonators provided only on one side of a sample in the same plane in such a way that long sides of the resonators are oriented in directions ($\theta$) different from each other, the $\Delta f \cdot \Delta P$ calculating unit (108) is configured to calculate $\Delta fr$ and $\Delta Pr$ after the anisotropy is canceled, and the absolute dry basis weight and moisture amount calculating unit (120) is configured to perform calculation using $\Delta fr$ and $\Delta Pr$ calculated by the $\Delta f \cdot \Delta P$ calculating unit (108) after the anisotropy is canceled.

Effects of the Invention

According to the present invention, when measuring a basis weight and a moisture amount (moisture percentage) of a sheet-like material such as paper using a microwave resonator, it is confirmed that measured values of the basis weight and the moisture can be separately and individually measured without being influenced by each other, and therefore, it is possible to perform the measurement safely without using radioactive rays.

BRIEF DESCRIPTION OF THE DRAWINGS

FIG. 1 is a block diagram illustrating a preferred embodiment of an apparatus of measuring basis weight and moisture amount.

FIG. 20 is a graph illustrating correlation between the measurement result of the basis weights using the microwave dielectric resonators and a measurement result of basis weights using a basis-weight moisture meter.

MODES FOR CARRYING OUT THE INVENTION

Figure 2A:
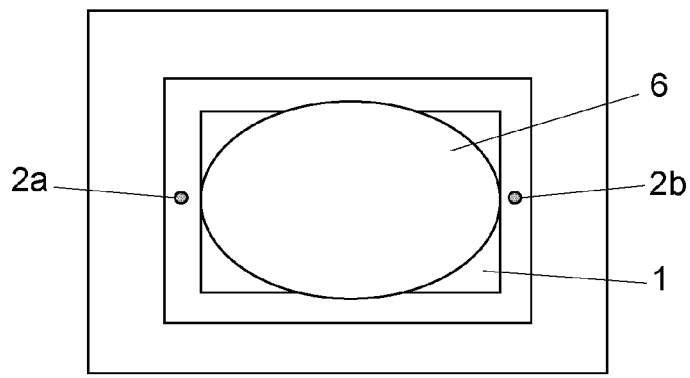
FIG. 2A is a plan view illustrating a dielectric resonator used in one example.
Figure 2B:
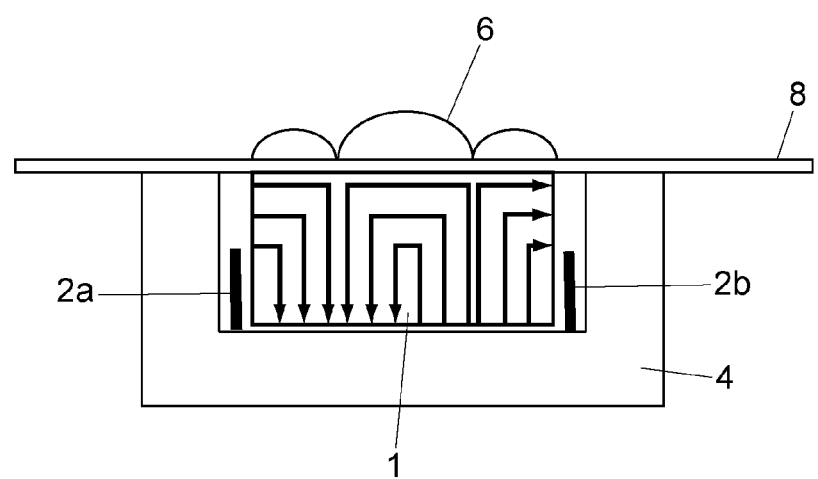
FIG. 2B is a vertical cross-sectional view of the resonator.
Figure 3:
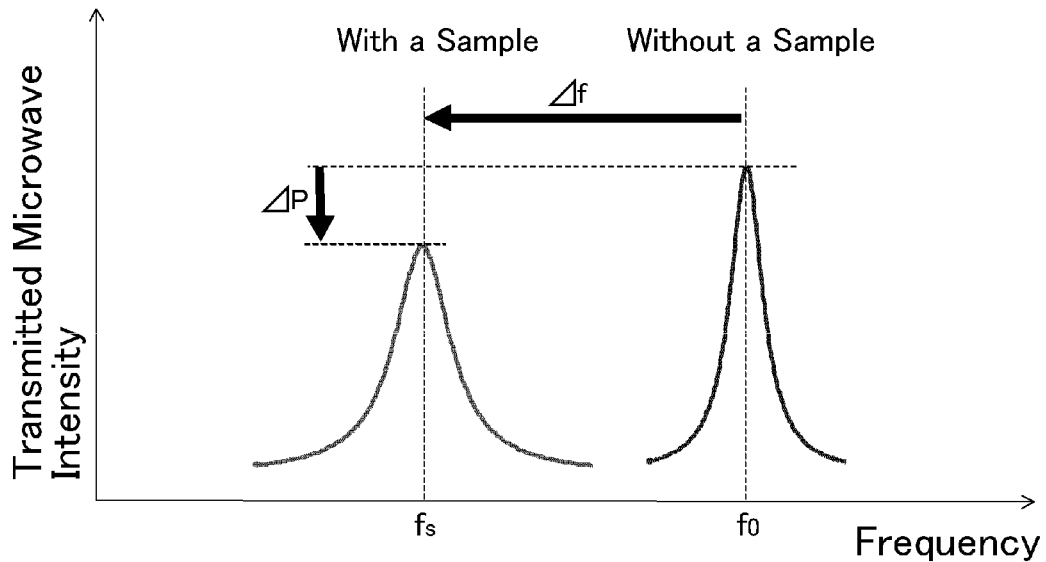
FIG. 3 is a waveform chart illustrating fluctuation in a resonant curve of the dielectric resonator depending on presence of samples.
Figure 4:
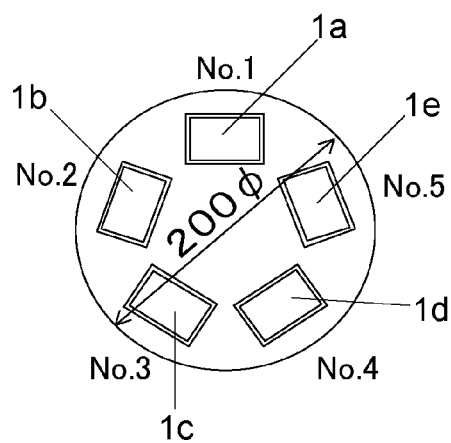
FIG. 4 is a plan view illustrating one example of an orientation meter measuring unit having five dielectric resonators provided.
Figure 5:
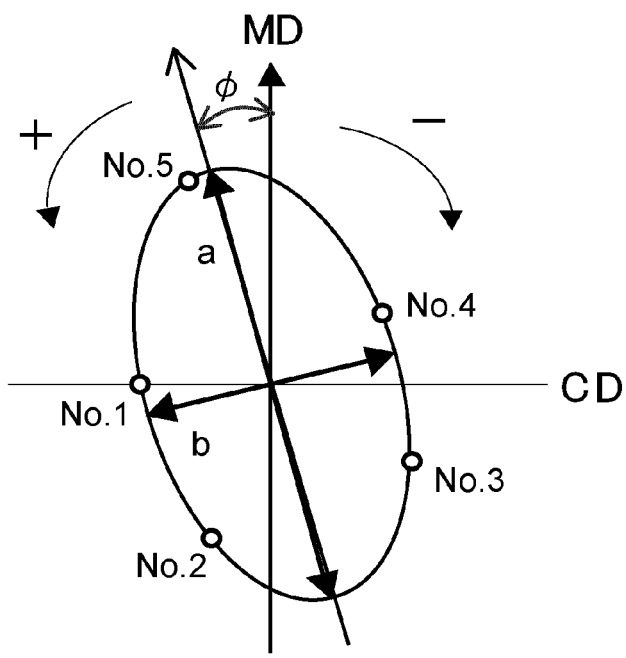
FIG. 5 is a diagram illustrating one example of an orientation pattern obtained from the five dielectric resonators illustrated in FIG. 4.
Figure 6:
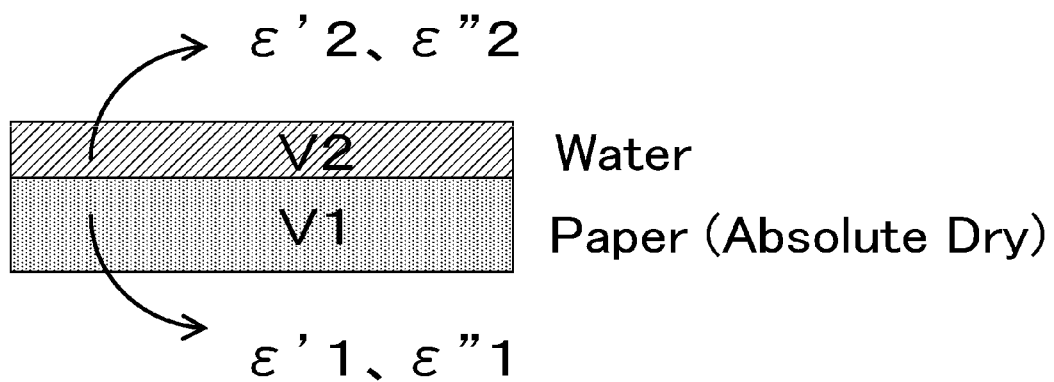
FIG. 6 is a cross-sectional view illustrating a moisture model.
Figure 7:
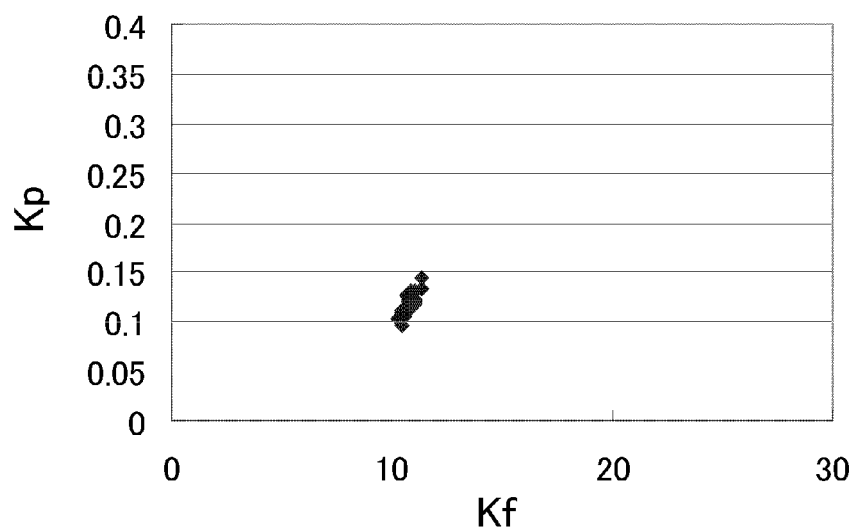
FIG. 7 is a graph illustrating constants Kf and Kp obtained by optimized material constants.
Figure 8:
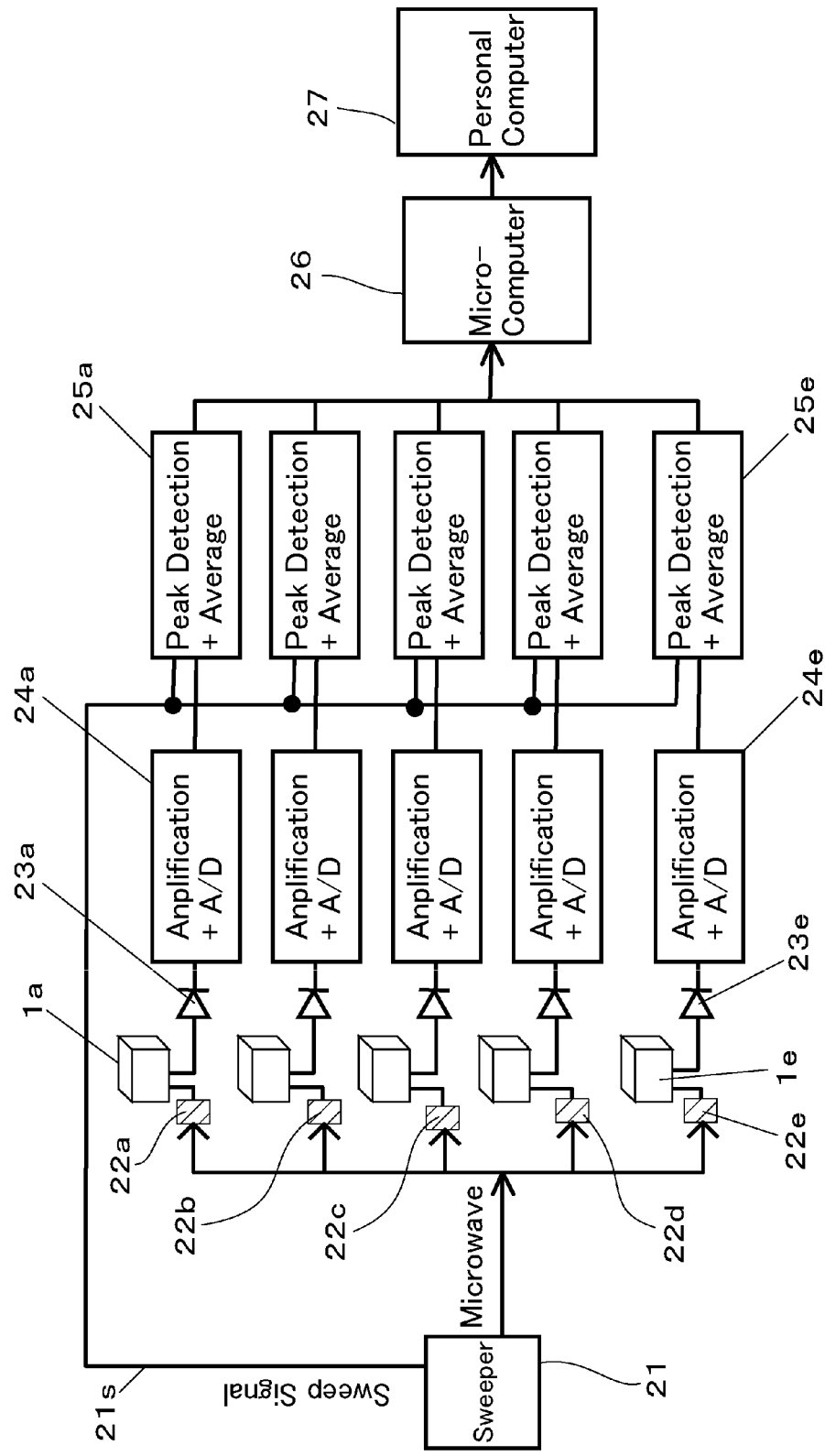
FIG. 8 is a block diagram illustrating circuits for processing signals from five dielectric resonators.

A specific example of a measurement apparatus will be described. This is an example realizing the present invention using an apparatus for measuring dielectric anisotropy of samples. Five dielectric resonators 1a-1e are provided, signals are processed by signal processing circuits illustrated by a block diagram in FIG. 8 based on a time chart illustrated in FIG. 9, and a resonance frequency and a resonance peak level are thereby measured.

Signals outputted from a microwave sweeper oscillator 21 as one example of microwave oscillation means are distributed to the dielectric resonators 1a-1e via isolators 22a-22e. Outputs from the resonators 1a-1e are converted into voltages by respective detector diodes 23a-23e, and inputted into respective peak detection and averaging procedure circuit units 25a-25e through respective amplification and A/D conversion circuit units 24a-24e.

Figure 9:
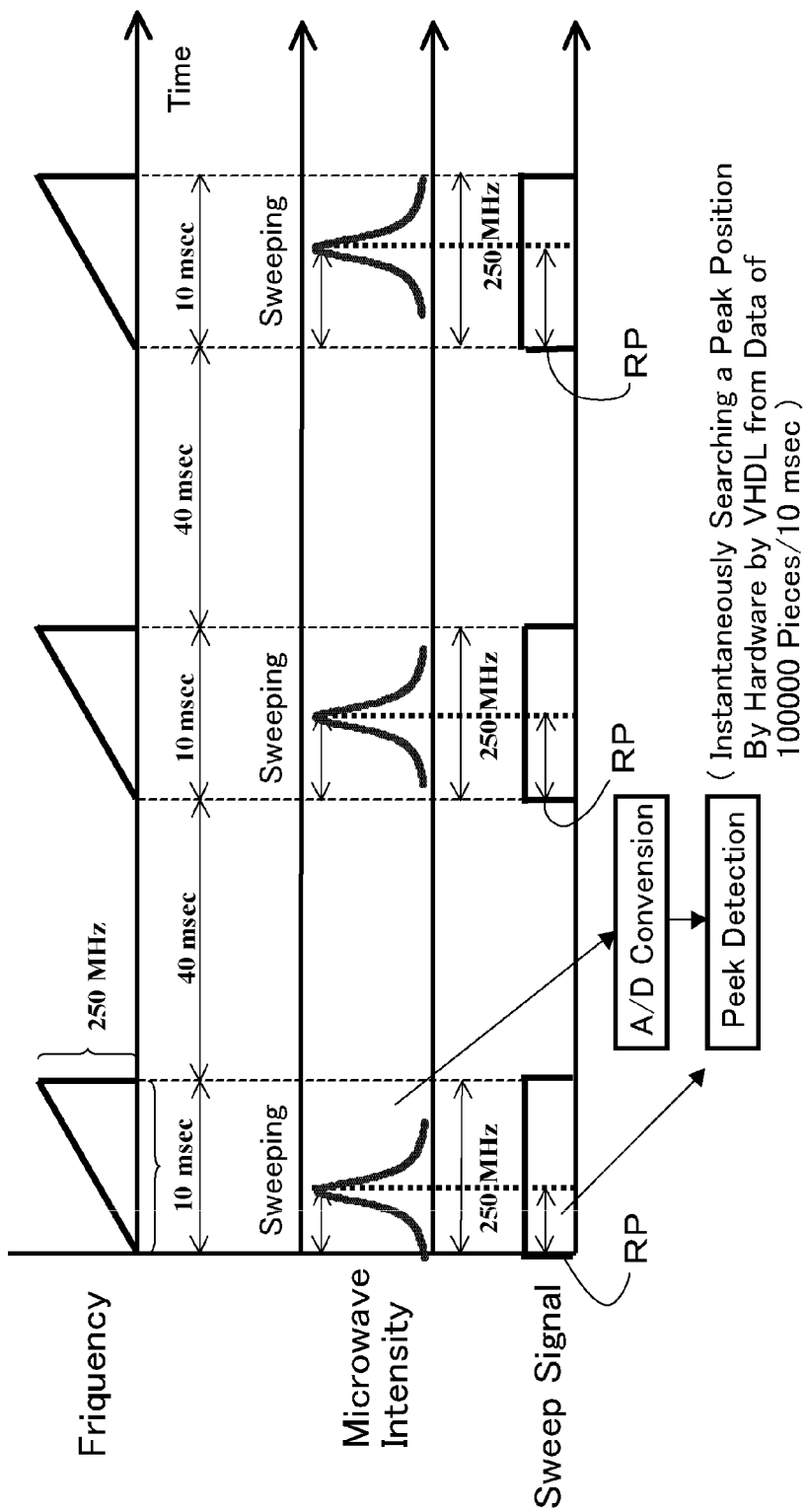
FIG. 9 is a time chart of the signal processing of the block diagram in FIG. 8.

Measurement of the resonance frequency is carried out as described below. As illustrated in FIG. 9, the microwave sweeper oscillator 21 sweeps a frequency. For example, it is possible to continuously increase the frequency by sweeping the frequency at 250 MHz in 10 msec centering 4 gigahertz. With the frequency sweep, in the peak detection and averaging procedure circuit units 25a-25e, a resonant curve is obtained based on a microwave transmission intensity. The peak detection and averaging procedure circuit units 25a-25e sense a start pulse portion of a sweep signal 21s, measure time until a resonance level reaches a peak, and obtain the resonance frequencies by proportional calculation based on the time.

According to this method, since sweep start timing can be sensed by the start pulse portion at which the sweep signal rises, the resonance frequency is measured by measuring the time from this time point until the resonance level reaches the peak level and by calculating based on a sweep speed at 250 MHz in 10 msec. This is repeated with a cycle of 50 msec, for example, and obtains a single resonance frequency by averaging results of 20 times of calculation. As described above, a single sweep time is as short as 10 msec, and the signals are amplified at high speed, and digital processing is performed at high speed.

Figure 10:
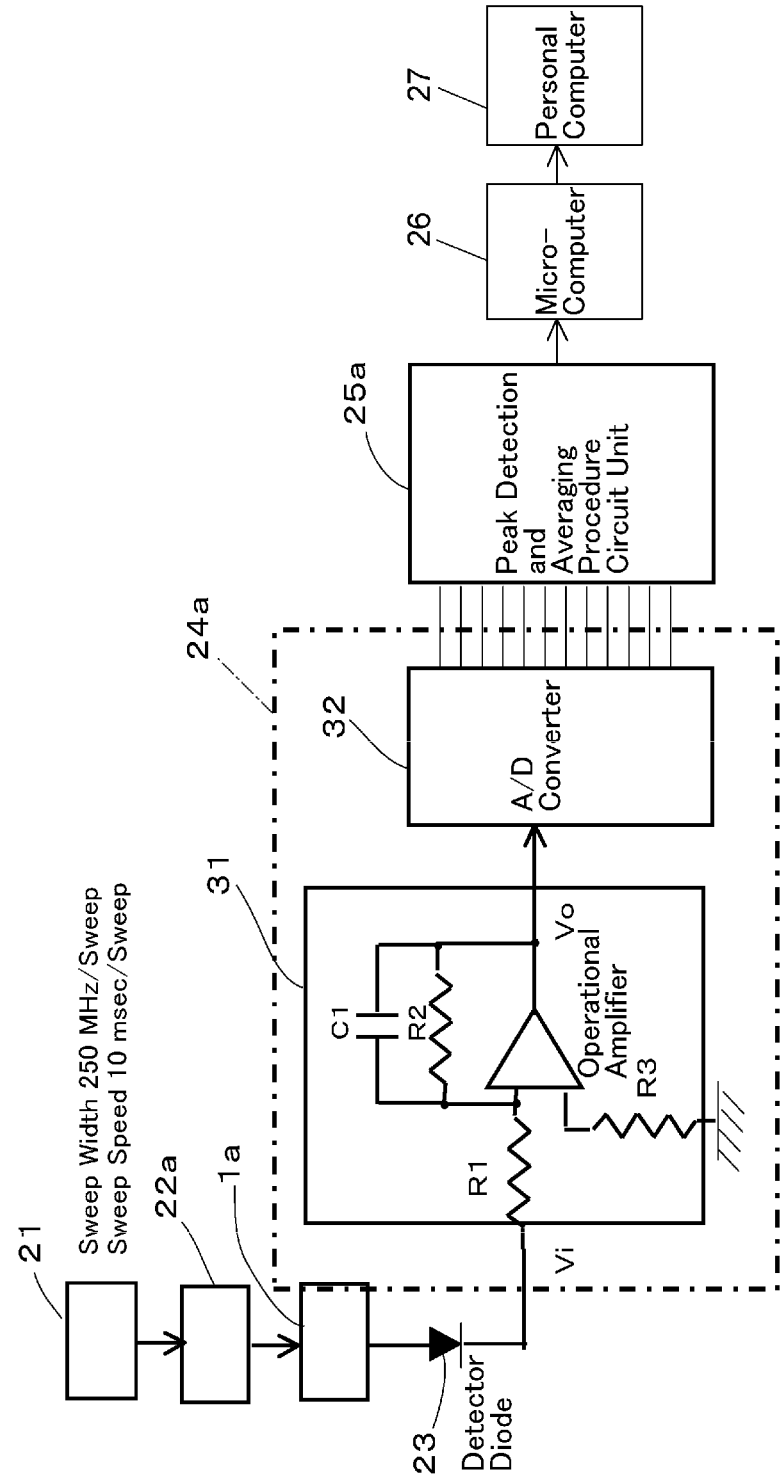
FIG. 10 is a block diagram illustrating a signal processing circuit for a single dielectric resonator out of the circuits illustrated in FIG. 8 in detail.

FIG. 10 illustrates a detecting circuit for a single dielectric resonator out of the circuit illustrated in FIG. 9 in detail. Other detecting circuits for other dielectric resonators are in the same configuration. One example of the amplification and A/D conversion circuit unit 24a described previously includes an amplify circuit 31 and an A/D converter unit LSI 32. A digital output from the amplification and A/D conversion circuit unit 24a enters the peak detection and averaging value procedure circuit unit 25a. One example of the peak detection and averaging procedure circuit unit 25a includes a peak detection LSI and an averaging procedure LSI. Accurately speaking, the peak detection LSI also includes a resonance peak level detection circuit. The LSI detects both of the resonance frequency and the resonance peak level as the resonance peak detection, and the averaging procedure LSI performs averaging procedure of the resonance frequency and the resonance peak level obtained in every sweep.

A microcomputer 26 is connected to subsequent stages of the peak detection and averaging procedure circuit units 25a-25e, and the signals from the dielectric resonator detecting systems are inputted to the microcomputer 26. The microcomputer 26 transmits the resonance frequencies and the resonance peak levels from the peak detection and averaging procedure circuit units 25a-25e as a whole to a personal computer 27 as a subsequent stage. The microcomputer 26 also has a control function of controlling to operate the amplification and A/D conversion circuit units 24a-24e, and the peak detection and averaging procedure circuit units 25a-25e for each dielectric resonator system.

The personal computer 27 serves a function of a data processing device 106 that calculates an output from the microcomputer 26 to obtain a basis weight and a moisture amount and displays or records the obtained values as data.

Here, referring to FIG. 10, in the amplification and A/D conversion circuit unit 24a, as an output after the amplification includes a ripple due to a noise, an RC circuit configured by a capacitor C1 and a resistance R2 are inserted into a feedback line of the amplify circuit 31, and a direct voltage with little fluctuation is obtained by absorbing and reducing a ripple voltage.

Functions of the data processing device realized by the personal computer 27 are as illustrated in FIG. 1.

Now, a case in which five rectangular dielectric resonators are used is more specifically described.

Figure 11:
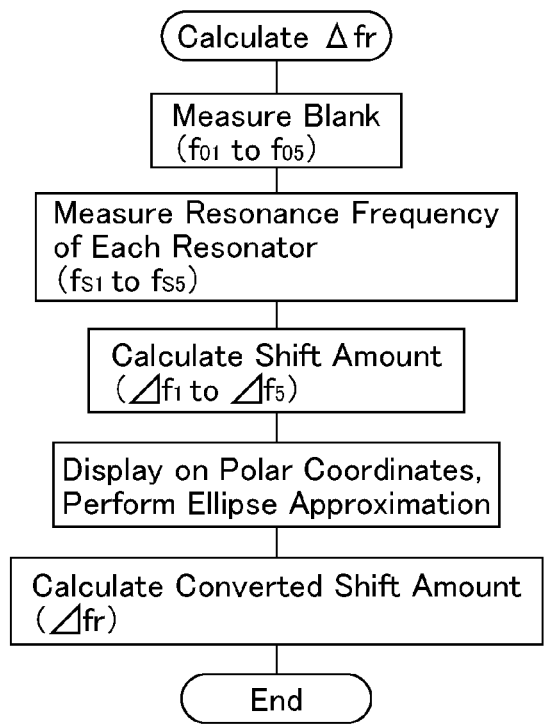
FIG. 11 is a flowchart illustrating steps of obtaining Δfr.

FIG. 11 shows steps of calculating Δfr.

Blank resonance frequencies are obtained for the dielectric resonators, and taken as $f_{o1}$, $f_{o2}$, $f_{o3}$, $f_{o4}$, and $f_{o5}$, respectively.

Resonance frequencies of the samples are obtained for the dielectric resonators, and taken as $f_{s1}$, $f_{s2}$, $f_{s3}$, $f_{s4}$, and $f_{s5}$, respectively.

Resonance frequency shift amounts Δf are calculated for the dielectric resonators, and taken as $\Delta f_1$, $\Delta f_2$, $\Delta f_3$, $\Delta f_4$, and $\Delta f_5$, respectively. Here, $$\Delta f_1 = f_{o1} - f_{s1},$$

$$\Delta f_2 = f_{o2} - f_{s2},$$

$$\Delta f_3 = f_{o3} - f_{s3},$$

$$\Delta f_4 = f_{o4} - f_{s4}, \text{ and}$$

$$\Delta f_5 = f_{o5} - f_{s5}.$$

Five points of Δf are displayed on a polar coordinate, and ellipse approximation is performed to calculate an area S of an ellipse. A radius of a circle having the same area as the area S of the ellipse is obtained, and the obtained value is taken as a converted shift amount Δfr.

$$\Delta fr = (S/\pi)^{1/2}$$

The value Δfr is a resonance frequency shift amount after canceling the anisotropy of the dielectric constant.

Figure 12:
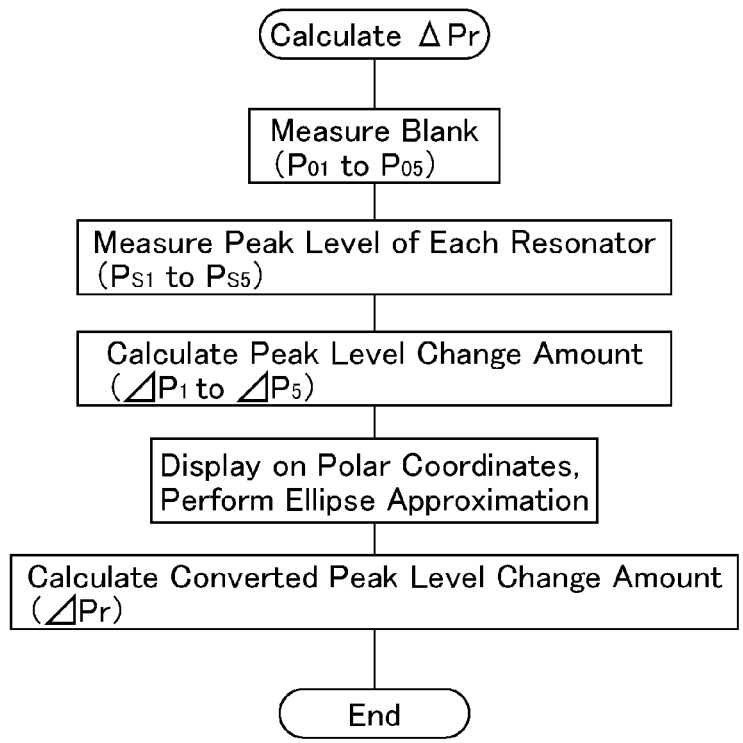
FIG. 12 is a flowchart illustrating steps of obtaining ΔPr.

Since peak levels do not have as much anisotropy as dielectric constants, a peak level change amount of a single dielectric resonator can be employed as ΔP regardless of the presence of samples, or an average value of the peak level change amounts of the five dielectric resonators can be employed as ΔP. Not a large error occurs even if such a value ΔP is employed. However, when further cancellation of the anisotropy is desired, it is possible to cancel the anisotropy in the same manner as the cancellation of the anisotropy of the dielectric constants. Steps in this case are illustrated in FIG. 12.

The peak levels $P_{o1}$ to $P_{o5}$ are measured at positions of the blank resonance frequencies of the dielectric resonators, respectively. The peak levels $P_{S1}$ to $P_{S5}$ are measured at positions of the resonance frequencies of the resonators with a sample, respectively. The peak level change amounts $\Delta P_1$ to $\Delta P_5$ are obtained respectively for the resonators. The values of $\Delta P_1$ to $\Delta P_5$ are displayed on the polar coordinate, and an area of an ellipse is obtained by the ellipse approximation processing. A radius of a circle having the same area as the area of the ellipse is obtained, and the radius of the circle is taken as a converted peak level change amount ΔPr after canceling the dielectric anisotropy of this sample.

Figure 13:
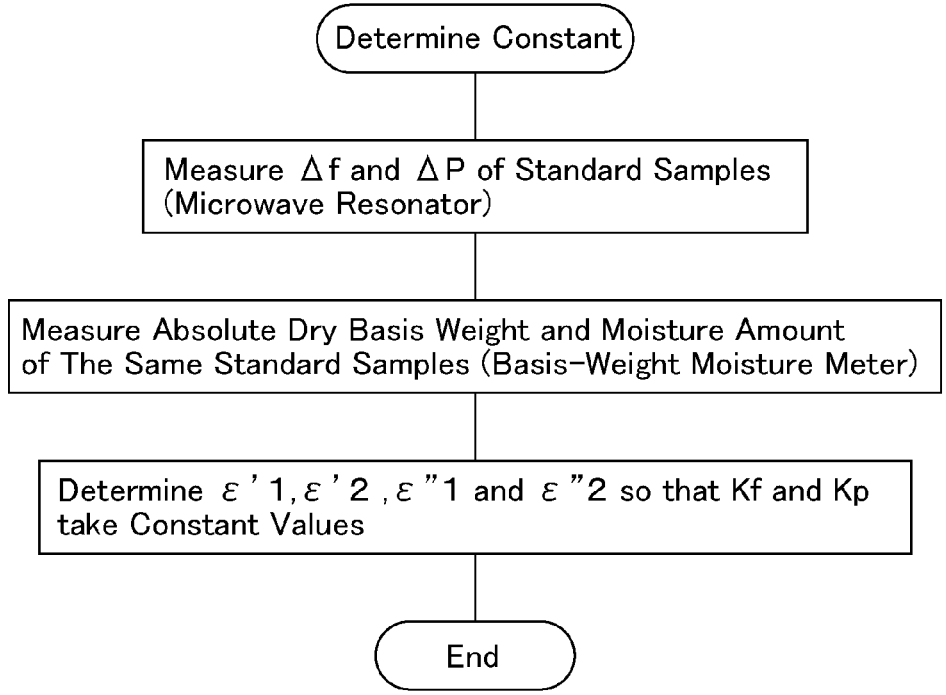
FIG. 13 is a flowchart illustrating steps of determining constants Kf and Kp, ∈'1 ∈'2, ∈"1, and ∈"2.

While the method of determining the constants Kf, Kp, ∈'1, ∈'2, ∈"1, and ∈"2 has already been described above, steps of this method are illustrated in FIG. 13 again.

For each of a plurality of standard samples having different basis weights or moisture amounts, a resonance frequency shift amount Δf and a peak level change amount ΔP are measured by a measurement apparatus using a microwave resonator, and an absolute dry basis weight (BD) and a moisture amount (WT) are measured by a basis-weight moisture meter.

Next, taking the absolute dry basis weight (BD) obtained by the basis-weight moisture meter as V1/β (β is a predetermined constant), and the moisture amount (WT) obtained by the basis-weight moisture meter as V2/γ (γ is a predetermined constant), and using Δf and ΔP thus obtained, ∈'1, ∈'2, ∈"1, and ∈"2 when variance values of Kf and Kp are smaller than a predetermined value in the relation of the expressions 1 and 2 or of the expressions 3 and 4 are obtained.

Figure 14:
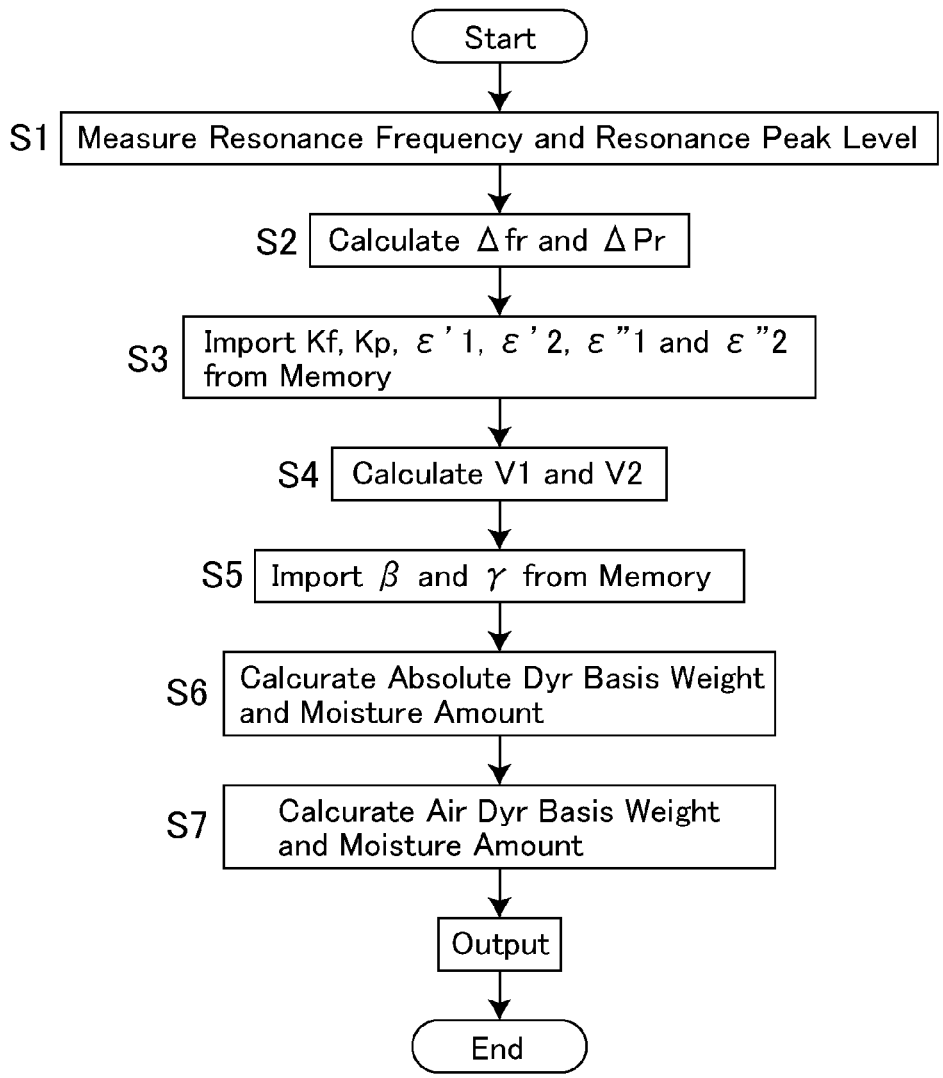
FIG. 14 is a flowchart illustrating one example of a series of a sample measurement operation.

An operation in the present example for obtaining the absolute dry basis weight and the moisture amount, in addition to the air dry basis weight and the moisture percentage, is illustrated in FIG. 14.

Using the microwave resonators that have measured the standard samples for determining the constants Kf, Kp, ∈'1, ∈'2, ∈"1, and ∈"2, the resonance frequencies and the resonance peak levels of the microwave resonators without a sample are measured. The resonance frequencies and the resonance peak levels of the same microwave resonators are measured by providing a sample (Step S1).

The resonance frequency shift amount Δfr and the resonance peak level change amount ΔP relating to the presence of the samples are obtained (Step S2).

The constants Kf, Kp, ∈'1, ∈'2, ∈"1, and ∈"2 are imported from a constant recording unit 114 of a memory, and V1 and V2 are calculated using the expressions 3 and 4 (Steps S3 and S4).

The constants β and γ are imported from the constant recording unit 114, and the absolute dry basis weight and the moisture amount are calculated using the expressions 5 and 6 (Steps S5 and S6).

Further, the air dry basis weight and the moisture percentage are calculated using the above expressions 7 and 8 (Step S7).

Measurement Example 1

Figure 15:
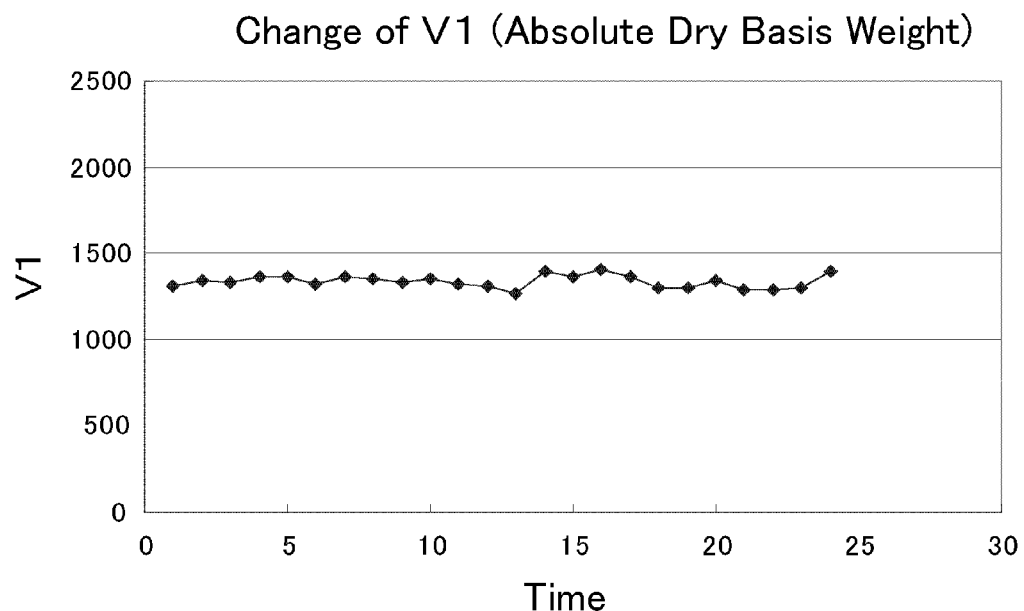
FIG. 15 is a graph illustrating a measurement result of basis weights of samples with a constant basis weight and different moisture amounts measured by an apparatus according to an example.
Figure 16:
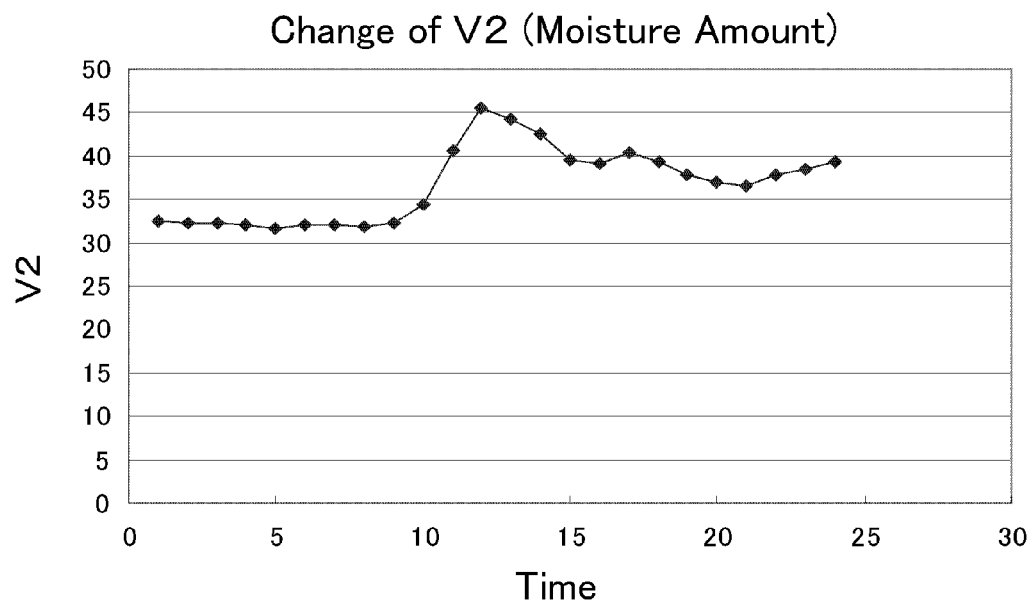
FIG. 16 is a graph illustrating a measurement result of moisture amounts of the same samples measured by the apparatus according to the example.

FIG. 15 and FIG. 16 illustrate calculation results of V1 (corresponds to the absolute dry basis weight) and V2 (corresponds to the moisture amount) in the above example when forcibly changing the moisture percentage from 2.7% to 5.8% in an actual paper machine. The results show that the absolute dry basis weight is substantially constant, and only the moisture amount increases. From this finding, according to this example, it is clear that the basis weight can be measured while eliminating an influence of the moisture using the microwave resonator.

Measurement Example 2

Figure 17:
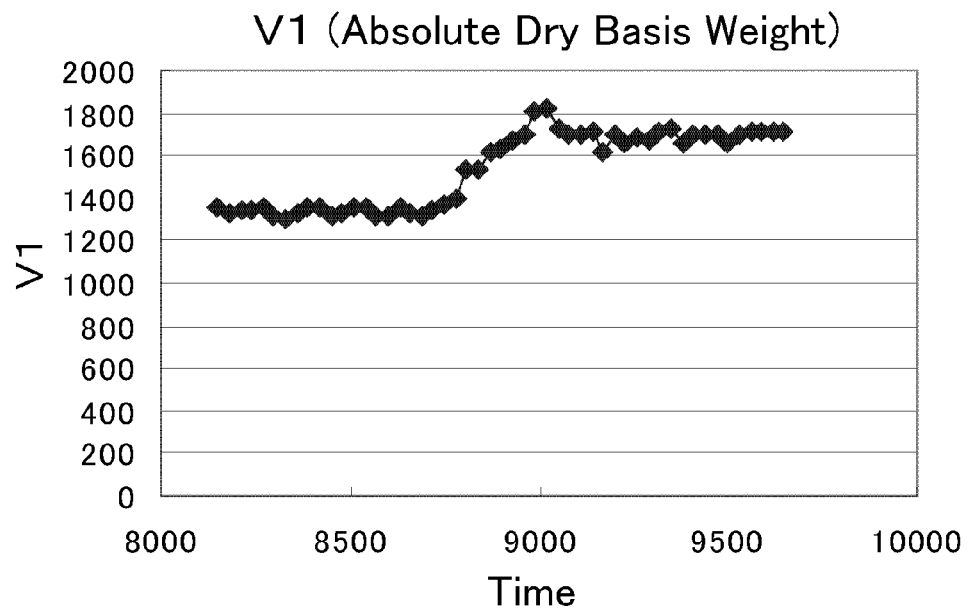
FIG. 17 is a graph illustrating a measurement result of basis weights of samples with a constant moisture percentage and different basis weights measured by the apparatus according to the example.
Figure 18:
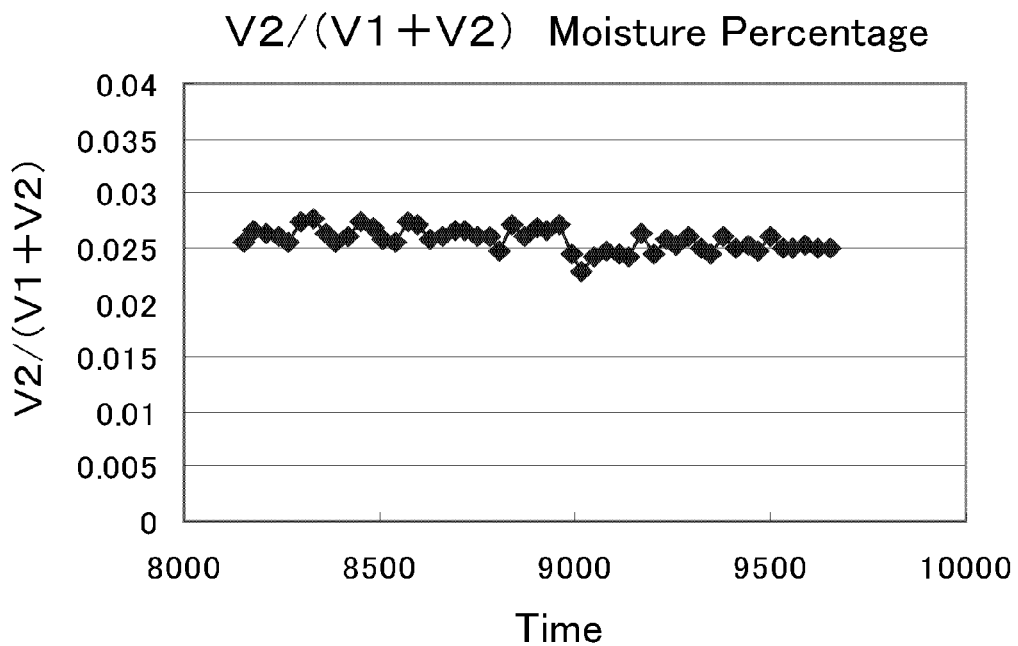
FIG. 18 is a graph illustrating a measurement result of moisture percentages of the same samples measured by the apparatus according to the example.
Figure 19:
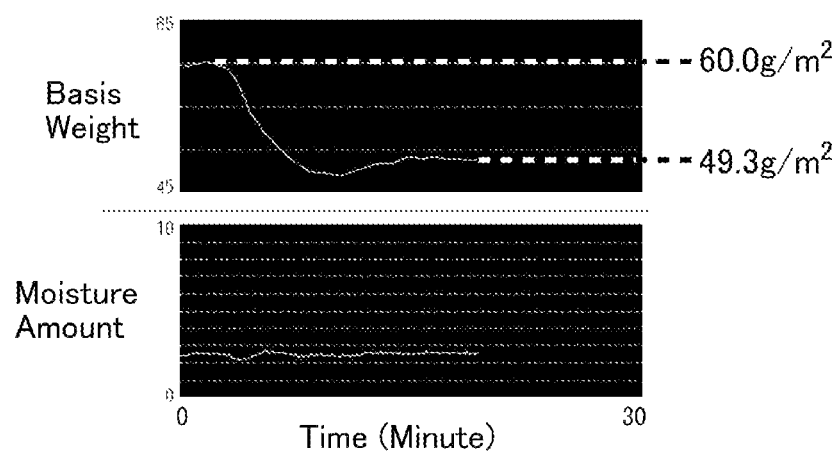
FIG. 19 is a chart illustrating an example of a measurement result of basis weights with a constant moisture percentage using microwave dielectric resonators.
Figure 21:
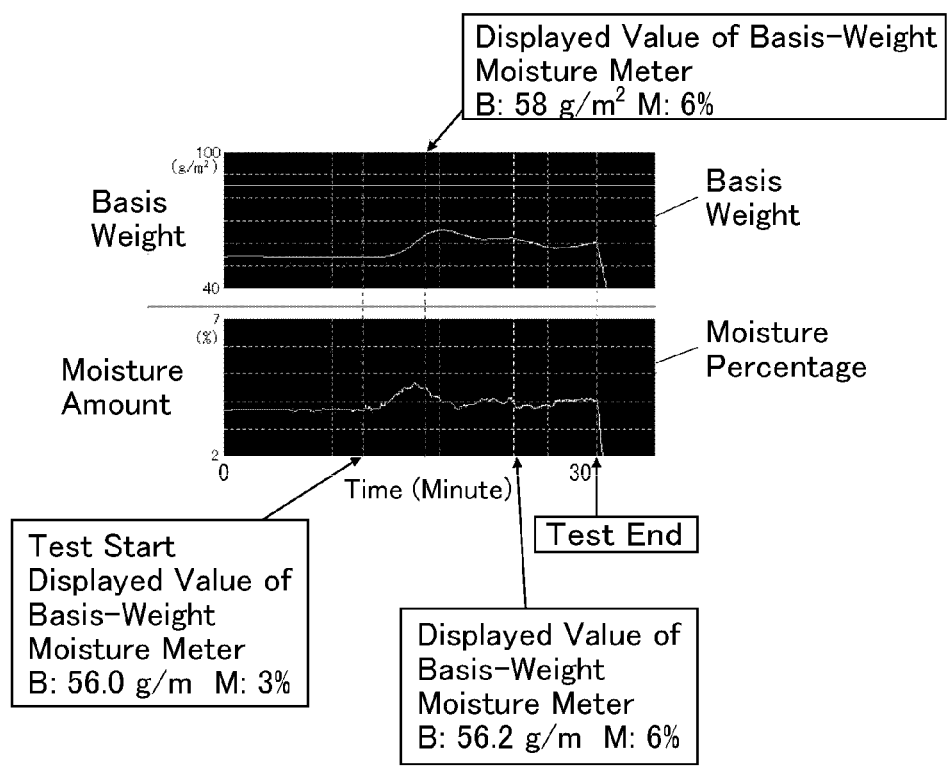
FIG. 21 is a chart illustrating a measurement result of basis weights with different moisture percentages using microwave dielectric resonators.

By contrast, in the actual paper machine, the basis weight is changed (measured basis weight 59.10 to 72.64 g/m$^2$) while keeping the moisture percentage of the sample substantially constant (3.0 to 2.9% in the measured value). FIG. 17 and FIG. 18 illustrate measurement results at this time in the above example. Also in this case, the changes in the sample are accurately reflected.

INDUSTRIAL APPLICABILITY

The present invention can be applied to a measurement of a basis weight and a moisture amount of a sheet-like material such as paper, non-woven fabric, and films.

DESCRIPTION OF REFERENCE CHARACTERS 1, 1a-1e Dielectric Resonator
2a, 2b Antenna
6 Evanescent Wave
8 Sample
27 Personal Computer
100 Microwave Resonator
102 Microwave Exciting Device
104 Detecting Device
106 Data Processing Device
108 $\Delta f \cdot \Delta P$ Calculating Unit
110 Basis-Weight Moisture Meter
112 First Constant Determining Unit
114 Constant Recording Unit
116 V1·V2 Calculating Unit
120 Absolute Dry Basis Weight and Moisture Amount Calculating Unit
122 Air Dry Basis Weight and Moisture Percentage Calculating Unit

The invention claimed is:

1. A method of measuring basis weight and moisture amount for calculating a basis weight and a moisture amount of a sample constituted by a paper sheet using a microwave resonator, the method comprising the steps S1 to S6 of;

(Step S1)
obtaining a resonance frequency and a resonance peak level of the microwave resonator in a case without a sample;

(Step S2)
obtaining a resonance frequency and a resonance peak level of the microwave resonator in the case where the sample is measured;

(Step S3)
obtaining a resonance frequency shift amount $\Delta f$ as a difference between the resonance frequency obtained in the step S1 and the resonance frequency obtained in the step S2;

(Step S4)
obtaining a peak level change amount $\Delta P$ as a difference between the resonance peak level obtained in the step S1 and the resonance peak level obtained in the step S2;

(Step S5)
obtaining V1 and V2 using expressions:

$$V1 = (\Delta f \cdot \in''2/Kf - \Delta p \cdot \in'2/Kp)/(\in'1 \cdot \in''2 - \in''1 \cdot \in'2) \quad (3); \text{ and}$$

$$V2 = (\Delta f \cdot \in''1/Kf - \Delta p \cdot \in'1/Kp)/(\in'1 \cdot \in''2 - \in'1 \cdot \in''2) \quad (4);$$

(Step S6)
obtaining an absolute dry basis weight and a moisture amount using expressions:

$$\text{Absolute Dry Basis Weight} = \beta \cdot V1 \quad (5); \text{ and}$$

$$\text{Moisture Amount} = \gamma \cdot V2 \quad (6),$$

wherein
V1: a volume of absolute dry paper under a certain condition;
V2: a volume of water under a certain condition;
Kf: a proportional constant for matching dimensions;
Kp: a proportional constant for matching dimensions;
$\in'1$: a dielectric constant of the absolute dry paper-1;
$\in'2$: a dielectric constant of the water;
$\in''1$: a dielectric loss factor of the absolute dry paper;
$\in''2$: a dielectric loss factor of the water; and
$\beta$, $\gamma$: proportional constants, and
the constants Kf, Kp, $\in'1$, $\in'2$, $\in''1$, and $\in''2$ are determined through the following steps A and B, and the constants $\beta$ and $\gamma$ are previously determined:

(Step A) for each of a plurality of standard samples having different values for one of the basis weight and the moisture amount, measuring the resonance frequency shift amount $\Delta f$ and the peak level change amount $\Delta P$ by a measurement apparatus using the microwave resonator through the steps S1 to S4; and (Step B) obtaining $\in'1$, $\in'2$, $\in''1$, and $\in''2$ when variance values of Kf and Kp are smaller than a predetermined value in the relation of the expressions (3) and (4), by taking $V1 = BD/\beta$ and $V2 = WT/\gamma$, BD being a predetermined absolute dry basis weight of each of the standard samples and WT being a predetermined moisture amount of each of the standard samples, and by using $\Delta f$ and $\Delta P$ obtained in the step A.

2. The method of measuring basis weight and moisture amount according to claim 1, wherein
an air dry basis weight and a moisture percentage are further obtained using the following expressions:

$$\text{Air Dry Basis Weight} = \text{Absolute Dry Basis Weight} + \text{Moisture Amount; and}$$

$$\text{Moisture Percentage} = \text{Moisture Amount} \times 100/\text{Air Dry Basis Weight}.$$

3. The method of measuring basis weight and moisture amount according to claim 1, further comprising:
providing a plurality of rectangular dielectric resonators constituting the microwave resonator only on one side of a sample in the same plane such that long sides of the resonators are oriented to directions ($\theta$) different from each other;

taking the directions ($\theta$) as angles $\theta$ and the resonance frequency shift amounts $\Delta f_1$ to $\Delta f_n$ of the resonators as r, plotting on a polar coordinate (r, $\theta$) in which an angle is $\theta$ and a distance from the point of origin is r to draw an ellipse by an ellipse approximation process, obtaining a radius $\Delta fr$ of a circle having an area identical to an area of the ellipse, and taking the obtained $\Delta fr$ as $\Delta f$; and obtaining peak level change amounts $\Delta P_1$ to $\Delta P_n$ of the resonators, and taking one of $\Delta Pr(A)$, $\Delta Pr(B)$, and $\Delta Pr(C)$ as $\Delta P$ according to claim 1, $\Delta Pr(A)$, $\Delta Pr(B)$, and $\Delta Pr(C)$ being:

(A) $\Delta Pr$ constituted by one of $\Delta P_2$ to $\Delta P_n$;
(B) $\Delta Pr$ constituted by an average value of $\Delta P_1$ to $\Delta P_n$; and
(C) $\Delta Pr$ constituted by a radius of a circle having an area identical to an area of an ellipse obtained by taking the directions ($\theta$) as angles $\theta$ and $\Delta P_1$ to $\Delta P_n$ as r, plotting on the polar coordinate (r, $\theta$) in which the angle is $\theta$ and a distance from the point of origin is r, and drawing the ellipse by the ellipse approximation process.

4. An apparatus of measuring basis weight and moisture amount comprising:
a microwave resonator;
a microwave exciting device configured to generate an electric field vector in the resonator;
a detecting device configured to detect one of a transmission energy and a reflected energy by the resonator; and
a data processing device configured to import resonance frequencies of the microwave resonator and peak levels at positions of the resonance frequencies in cases without a sample and with a sample from the detecting device, and to calculate a basis weight and a moisture amount of the sample, wherein the data processing device includes:
- a $\Delta f \cdot \Delta P$ calculating unit configured to calculate a resonance frequency shift amount $\Delta f$ and a peak level change amount $\Delta P$ respectively based on the resonance frequencies and the peak levels imported from the detecting device;
- a first constant determining unit configured to determine constants Kf, Kp, $\in'1$, $\in'2$, $\in''1$, and $\in''2$ by obtaining $\in'1$, $\in'2$, $\in''1$, and $\in''2$ when variance values of Kf and Kp are smaller than a predetermined value in the relation of the expressions (3) and (4) according to claim 1, using $\Delta f$ and $\Delta P$ obtained by the $\Delta f \cdot \Delta P$ calculating unit when each of a plurality of standard samples having different values for one of the basis weight and the moisture amount is measured by the microwave resonator, and taking a predetermined absolute dry basis weight of each of the standard samples as $V1/\beta$ and a predetermined moisture amount of each of the standard samples as $V2/\gamma$ by measuring the standard samples;
- a constant recording unit configured to record the constants Kf, Kp, $\in'1$, $\in'2$, $\in''1$, and $\in''2$ determined by the first constant determining unit (112), and the proportional constants $\beta$ and $\gamma$;
- a V1·V2 calculating unit configured to calculate V1 and V2 based on the expressions (3) and (4) according to claim 1 using the constants Kf, Kp, $\in'1$, $\in'2$, $\in''1$, and $\in''2$ recorded in the constant recording unit, and $\Delta f$ and $\Delta P$ obtained by the $\Delta f \cdot \Delta P$ calculating unit when the samples are measured by the microwave resonator; and
- an absolute dry basis weight and moisture amount calculating unit configured to calculate an absolute dry basis weight and a moisture amount based on the expressions (5) and (6) according to claim 1 from V1 and V2 obtained by the V1·V2 calculating unit when the samples are measured by the microwave resonator and the proportional constants $\beta$ and $\gamma$ recorded in the constant recording unit.

5. The apparatus of measuring basis weight and moisture amount according to claim 4, further comprising:
an air dry basis weight and moisture percentage calculating unit configured to calculate an air dry basis weight and a moisture percentage based on the expressions according to claim 2 from the absolute dry basis weight and the moisture amount obtained by the absolute dry basis weight and moisture amount calculating unit.

6. The apparatus of measuring basis weight and moisture amount according to claim 4, wherein
the microwave resonator is constituted by a plurality of rectangular dielectric resonators provided only on one side of a sample in the same plane such that long sides of the resonators are oriented to directions ($\theta$) different from each other,
the $\Delta f \cdot \Delta P$ calculating unit is configured to calculate $\Delta fr$ and $\Delta Pr$ according to claim 3, and
the absolute dry basis weight and moisture amount calculating unit is configured to perform calculation using $\Delta fr$ and $\Delta Pr$ calculated by the $\Delta f \cdot \Delta P$ calculating unit.

7. The method of measuring basis weight and moisture amount according to claim 2, further comprising:
providing a plurality of rectangular dielectric resonators constituting the microwave resonator only on one side of a sample in the same plane such that long sides of the resonators are oriented to directions ($\theta$) different from each other;
taking the directions ($\theta$) as angles $\theta$ and the resonance frequency shift amounts $\Delta f_1$ to $\Delta f_r$, of the resonators as r, plotting on a polar coordinate (r, $\theta$) in which an angle is $\theta$ and a distance from the point of origin is r to draw an ellipse by an ellipse approximation process, obtaining a radius $\Delta fr$ of a circle having an area identical to an area of the ellipse, and taking the obtained $\Delta fr$ as $\Delta f$ according to claim 1; and
obtaining peak level change amounts $\Delta P_1$ to $\Delta P_n$ of the resonators, and taking one of $\Delta Pr(A)$, $\Delta Pr(B)$, and $\Delta Pr(C)$ as $\Delta P$ according to claim 1, $\Delta Pr(A)$, $\Delta Pr(B)$, and $\Delta Pr(C)$ being:
(A) $\Delta Pr$ constituted by one of $\Delta P_1$ to $\Delta P_n$;
(B) $\Delta Pr$ constituted by an average value of $\Delta P_1$ to $\Delta P_n$; and
(C) $\Delta Pr$ constituted by a radius of a circle having an area identical to an area of an ellipse obtained by taking the directions ($\theta$) as angles $\theta$ and $\Delta P_1$ to $\Delta P_n$ as r, plotting on the polar coordinate (r, $\theta$) in which the angle is $\theta$ and a distance from the point of origin is r, and drawing the ellipse by the ellipse approximation process.

8. The apparatus of measuring basis weight and moisture amount according to claim 5, wherein
the microwave resonator is constituted by a plurality of rectangular dielectric resonators provided only on one side of a sample in the same plane such that long sides of the resonators are oriented to directions ($\theta$) different from each other,
the $\Delta f \cdot \Delta P$ calculating unit is configured to calculate $\Delta fr$ and $\Delta Pr$ according to claim 3, and
the absolute dry basis weight and moisture amount calculating unit is configured to perform calculation using $\Delta fr$ and $\Delta Pr$ calculated by the $\Delta f \cdot \Delta P$ calculating unit.

9. The apparatus of measuring basis weight and moisture amount according to claim 4, wherein
the microwave resonator is constituted by a plurality of rectangular dielectric resonators provided only on one side of a sample in the same plane such that long sides of the resonators are oriented to directions ($\theta$) different from each other,
the $\Delta f \cdot \Delta P$ calculating unit is configured to calculate $\Delta fr$ and $\Delta Pr$ according to claim 7, and
the absolute dry basis weight and moisture amount calculating unit is configured to perform calculation using $\Delta fr$ and $\Delta Pr$ calculated by the $\Delta f \cdot \Delta P$ calculating unit.

10. The apparatus of measuring basis weight and moisture amount according to claim 5, wherein
the microwave resonator is constituted by a plurality of rectangular dielectric resonators provided only on one side of a sample in the same plane such that long sides of the resonators are oriented to directions ($\theta$) different from each other,
the $\Delta f \cdot \Delta P$ calculating unit is configured to calculate $\Delta fr$ and $\Delta Pr$ according to claim 7, and
the absolute dry basis weight and moisture amount calculating unit is configured to perform calculation using $\Delta fr$ and $\Delta Pr$ calculated by the $\Delta f \cdot \Delta P$ calculating unit.

* * * * *